(12) United States Patent
Christianson et al.

(10) Patent No.: US 8,372,112 B2
(45) Date of Patent: Feb. 12, 2013

(54) CLOSURE DEVICES, RELATED DELIVERY METHODS, AND RELATED METHODS OF USE

(75) Inventors: Mark R. Christianson, Darwin, MN (US); Scott A. Olson, Zimmerman, MN (US); Edward J. Anderson, Hopkins, MN (US); Philip J. Haarstad, Chanhassen, MN (US); Douglas J. Krone, Rogers, MN (US); Dennis W. Wahr, Ann Arbor, MI (US); David J. Blaeser, Champlin, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 1725 days.

(21) Appl. No.: 10/934,735

(22) Filed: Sep. 7, 2004

(65) Prior Publication Data

US 2006/0009800 A1   Jan. 12, 2006

Related U.S. Application Data

(63) Continuation-in-part of application No. 10/411,152, filed on Apr. 11, 2003, now abandoned.

(51) Int. Cl.
*A61B 17/08* (2006.01)
(52) U.S. Cl. ........................................ 606/213; 606/215
(58) Field of Classification Search ................... 606/1, 5, 606/151, 200, 213, 216, 217, 218
See application file for complete search history.

(56) References Cited

U.S. PATENT DOCUMENTS

| | | |
|---|---|---|
| 3,221,746 A | 12/1965 | Noble |
| 3,402,710 A | 9/1968 | Paleschuck |
| 3,540,431 A | 11/1970 | Uddin |
| 3,620,212 A | 11/1971 | Fannon |
| 3,638,388 A | 2/1972 | Kelly |
| 3,638,652 A | 2/1972 | Kelley |
| 3,657,744 A | 4/1972 | Ersek |
| 3,844,302 A | 10/1974 | Klein |
| 3,874,388 A | 4/1975 | King et al. |
| 4,007,743 A | 2/1977 | Blake |

(Continued)

FOREIGN PATENT DOCUMENTS

| | | |
|---|---|---|
| AU | 79531 | 3/1975 |
| AU | 670239 | 1/1994 |

(Continued)

OTHER PUBLICATIONS

PCT Search Report of PCT/US 04/010607.

(Continued)

*Primary Examiner* — Tuan V Nguyen
(74) *Attorney, Agent, or Firm* — Lerner, David, Littenberg, Krumholz & Mentlik, LLP

(57) ABSTRACT

A closure device for sealing a patent foramen ovale (PFO) in the heart includes a left atrial anchor adapted to be placed in a left atrium of the heart, a right atrial anchor adapted to be placed in a right atrium of the heart, and a flexible elongate member adapted to extend through the passageway and connect the left and right atrial anchors. A delivery system for delivering the closure device includes a lock push tube for moving a lock along the elongate member and a wire release tube surrounding a wire for controlling movement of the right atrial anchor along the elongate member. The lock push tube and the wire release tube extend in a side-by-side relationship. A handle includes knobs for controlling the lock push tube and the wire. A device for retrieving a mis-deployed closure device includes a shaft portion and an expandable retrieval portion.

51 Claims, 33 Drawing Sheets

U.S. PATENT DOCUMENTS

| | | | |
|---|---|---|---|
| 4,041,931 A | 8/1977 | Elliott et al. | |
| 4,083,162 A | 4/1978 | Regan et al. | |
| 4,214,587 A | 7/1980 | Sakura, Jr. | |
| 4,309,776 A | 1/1982 | Berguer | |
| 4,341,218 A | 7/1982 | Ü | |
| 4,368,736 A | 1/1983 | Kaster | |
| 4,485,816 A | 12/1984 | Krumme | |
| 4,503,569 A | 3/1985 | Dotter | |
| 4,592,754 A | 6/1986 | Gupte et al. | |
| 4,603,693 A | 8/1986 | Conta et al. | |
| 4,617,932 A | 10/1986 | Kornberg | |
| 4,619,246 A | 10/1986 | Molgaard-Nielsen et al. | |
| 4,629,451 A | 12/1986 | Winters et al. | |
| 4,649,922 A | 3/1987 | Wiktor | |
| 4,665,906 A | 5/1987 | Jervis | |
| 4,681,588 A | 7/1987 | Ketharanathan | |
| 4,710,192 A | 12/1987 | Liotta et al. | |
| 4,733,665 A | 3/1988 | Palmaz | |
| 4,739,762 A | 4/1988 | Palmaz | |
| 4,748,982 A | 6/1988 | Horzewski et al. | |
| 4,776,337 A | 10/1988 | Palmaz | |
| 4,787,899 A | 11/1988 | Lazarus | |
| 4,826,487 A | 5/1989 | Winter | |
| 4,832,055 A | 5/1989 | Palestrant | |
| 4,836,204 A | 6/1989 | Landymore et al. | |
| 4,917,089 A | 4/1990 | Sideris | |
| 4,921,484 A | 5/1990 | Hillstead | |
| 4,994,069 A | 2/1991 | Ritchart | |
| 5,041,082 A | 8/1991 | Shiber | |
| 5,041,090 A | 8/1991 | Scheglov et al. | |
| 5,042,707 A | 8/1991 | Taheri | |
| 5,052,386 A | 10/1991 | Fischer, Jr. | |
| 5,064,435 A | 11/1991 | Porter | |
| 5,067,489 A | 11/1991 | Lind | |
| 5,067,957 A | 11/1991 | Jervis | |
| 5,078,736 A | 1/1992 | Behl | |
| 5,098,440 A | 3/1992 | Hillstead | |
| 5,104,399 A | 4/1992 | Lazarus | |
| 5,108,420 A | 4/1992 | Marks | |
| 5,122,136 A | 6/1992 | Guglielmi et al. | |
| 5,122,156 A | 6/1992 | Granger et al. | |
| 5,135,467 A | 8/1992 | Citron | |
| 5,147,370 A | 9/1992 | McNamara et al. | |
| 5,171,233 A | 12/1992 | Amplatz et al. | |
| 5,171,259 A * | 12/1992 | Inoue | 606/213 |
| 5,176,692 A | 1/1993 | Wilk et al. | |
| 5,190,536 A | 3/1993 | Wood et al. | |
| 5,192,301 A | 3/1993 | Kamiya et al. | |
| 5,207,695 A | 5/1993 | Trout, III | |
| 5,211,658 A | 5/1993 | Clouse | |
| 5,211,683 A | 5/1993 | Maginot | |
| 5,234,447 A | 8/1993 | Kaster et al. | |
| 5,234,458 A | 8/1993 | Metals | |
| 5,246,445 A | 9/1993 | Yachia et al. | |
| 5,254,133 A | 10/1993 | Seid | |
| 5,258,000 A | 11/1993 | Gianturco | |
| 5,258,042 A | 11/1993 | Mehta | |
| 5,275,622 A | 1/1994 | Lazarus et al. | |
| 5,284,486 A | 2/1994 | Kotula et al. | |
| 5,284,488 A | 2/1994 | Sideris | |
| 5,304,184 A | 4/1994 | Hathaway et al. | |
| 5,304,220 A | 4/1994 | Maginot | |
| 5,306,234 A | 4/1994 | Johnson | |
| 5,316,023 A | 5/1994 | Palmaz et al. | |
| 5,334,217 A | 8/1994 | Das | |
| 5,350,398 A | 9/1994 | Pavcnik et al. | |
| 5,350,399 A | 9/1994 | Erlebacher et al. | |
| 5,354,309 A | 10/1994 | Schnepp-Pesch et al. | |
| 5,354,336 A | 10/1994 | Kelman et al. | |
| 5,360,443 A | 11/1994 | Barone et al. | |
| 5,366,462 A | 11/1994 | Kaster et al. | |
| 5,375,612 A | 12/1994 | Cottenceau et al. | |
| 5,385,562 A | 1/1995 | Adams et al. | |
| 5,387,235 A | 2/1995 | Chuter | |
| 5,391,156 A | 2/1995 | Hildwein et al. | |
| 5,397,345 A | 3/1995 | Lazarus | |
| 5,397,355 A | 3/1995 | Marin et al. | |
| 5,417,699 A | 5/1995 | Klein et al. | |
| 5,425,744 A | 6/1995 | Fagan et al. | |
| 5,433,497 A | 7/1995 | Koenig | |
| 5,433,727 A * | 7/1995 | Sideris | 606/213 |
| 5,443,454 A | 8/1995 | Tanabe et al. | |
| 5,443,478 A | 8/1995 | Purdy | |
| 5,443,497 A | 8/1995 | Venbrux | |
| 5,451,235 A | 9/1995 | Lock et al. | |
| 5,452,733 A | 9/1995 | Sterman et al. | |
| 5,456,693 A | 10/1995 | Conston et al. | |
| 5,456,712 A | 10/1995 | Maginot | |
| 5,464,408 A | 11/1995 | Duc | |
| 5,466,242 A | 11/1995 | Mori | |
| 5,478,354 A | 12/1995 | Tovey et al. | |
| 5,486,193 A | 1/1996 | Bourne et al. | |
| 5,489,295 A | 2/1996 | Piplani et al. | |
| 5,490,856 A | 2/1996 | Person et al. | |
| 5,496,365 A | 3/1996 | Sgro | |
| 5,507,769 A | 4/1996 | Marin et al. | |
| 5,522,790 A | 6/1996 | Moll et al. | |
| 5,522,822 A | 6/1996 | Phelps et al. | |
| 5,522,836 A | 6/1996 | Palermo | |
| 5,522,880 A | 6/1996 | Barone et al. | |
| 5,522,882 A | 6/1996 | Gaterud et al. | |
| 5,527,292 A | 6/1996 | Adams et al. | |
| 5,527,322 A | 6/1996 | Klein et al. | |
| 5,527,338 A | 6/1996 | Purdy | |
| 5,545,214 A | 8/1996 | Stevens | |
| 5,562,728 A | 10/1996 | Lazarus et al. | |
| 5,578,045 A * | 11/1996 | Das | 606/151 |
| 5,597,378 A | 1/1997 | Jervis | |
| 5,607,444 A | 3/1997 | Lam | |
| 5,614,204 A | 3/1997 | Cochrum | |
| 5,617,878 A | 4/1997 | Taheri | |
| 5,618,311 A | 4/1997 | Gryskiewicz | |
| 5,634,696 A | 6/1997 | Hart | |
| 5,634,936 A | 6/1997 | Linden et al. | |
| 5,645,558 A | 7/1997 | Horton | |
| 5,653,747 A | 8/1997 | Dereume | |
| 5,669,933 A | 9/1997 | Simon et al. | |
| 5,676,670 A | 10/1997 | Kim | |
| 5,681,336 A | 10/1997 | Clement et al. | |
| 5,693,067 A | 12/1997 | Purdy | |
| 5,693,083 A | 12/1997 | Baker et al. | |
| 5,695,504 A | 12/1997 | Gifford, III et al. | |
| 5,702,412 A | 12/1997 | Popov et al. | |
| 5,702,421 A | 12/1997 | Schneidt | |
| 5,709,224 A | 1/1998 | Behl et al. | |
| 5,709,707 A | 1/1998 | Lock et al. | |
| 5,725,552 A | 3/1998 | Kotula et al. | |
| 5,725,568 A | 3/1998 | Hastings | |
| 5,733,294 A | 3/1998 | Forber et al. | |
| 5,735,290 A | 4/1998 | Sterman et al. | |
| 5,735,893 A | 4/1998 | Lau et al. | |
| 5,741,297 A | 4/1998 | Simon | |
| 5,749,894 A | 5/1998 | Engelson | |
| 5,755,778 A | 5/1998 | Kleshinski | |
| 5,775,778 A | 5/1998 | Kleshinski | |
| 5,766,219 A | 6/1998 | Horton | |
| 5,776,097 A | 7/1998 | Massoud | |
| 5,776,162 A | 7/1998 | Kleshinski | |
| 5,782,860 A | 7/1998 | Epstein et al. | |
| 5,797,960 A | 8/1998 | Stevens et al. | |
| 5,830,228 A | 11/1998 | Knapp et al. | |
| 5,833,698 A | 11/1998 | Hinchliffe et al. | |
| 5,836,968 A | 11/1998 | Simon et al. | |
| 5,840,064 A | 11/1998 | Liprie | |
| 5,843,118 A | 12/1998 | Sepetka et al. | |
| 5,843,164 A | 12/1998 | Frantzen et al. | |
| 5,843,170 A | 12/1998 | Ahn | |
| 5,843,175 A | 12/1998 | Frantzen | |
| 5,843,176 A | 12/1998 | Weier | |
| 5,846,261 A | 12/1998 | Kotula et al. | |
| 5,849,005 A | 12/1998 | Garrison et al. | |
| 5,853,419 A | 12/1998 | Imran | |
| 5,853,422 A | 12/1998 | Huebsch et al. | |
| 5,861,003 A | 1/1999 | Latson et al. | |
| 5,865,791 A | 2/1999 | Whayne et al. | |
| 5,868,762 A | 2/1999 | Cragg et al. | |
| 5,879,366 A | 3/1999 | Shaw et al. | |

| Patent/Pub No. | Date | Name |
|---|---|---|
| 5,885,258 A | 3/1999 | Sachdeva |
| 5,891,558 A | 4/1999 | Bell et al. |
| 5,904,680 A | 5/1999 | Kordis et al. |
| 5,904,703 A | 5/1999 | Gilson |
| 5,906,207 A | 5/1999 | Shen |
| 5,910,155 A | 6/1999 | Ratcliff et al. |
| 5,919,200 A | 7/1999 | Stambaugh et al. |
| 5,921,995 A | 7/1999 | Kleshinski |
| 5,922,022 A | 7/1999 | Nash et al. |
| 5,935,148 A | 8/1999 | Villar et al. |
| 5,944,738 A | 8/1999 | Amplatz et al. |
| 5,976,159 A | 11/1999 | Bolduc et al. |
| 5,976,178 A | 11/1999 | Goldsteen et al. |
| 6,013,190 A | 1/2000 | Berg et al. |
| 6,021,340 A | 2/2000 | Randolph et al. |
| 6,024,756 A | 2/2000 | Huebsch et al. |
| 6,026,814 A | 2/2000 | LaFontaine et al. |
| 6,035,856 A | 3/2000 | LaFontaine et al. |
| 6,036,702 A | 3/2000 | Bachinski et al. |
| 6,036,716 A | 3/2000 | Kruchinin et al. |
| 6,074,416 A | 6/2000 | Berg et al. |
| 6,076,012 A | 6/2000 | Swanson et al. |
| 6,079,414 A | 6/2000 | Roth |
| 6,080,182 A | 6/2000 | Shaw et al. |
| 6,113,612 A | 9/2000 | Swanson et al. |
| 6,120,432 A | 9/2000 | Sullivan et al. |
| 6,123,715 A | 9/2000 | Amplatz |
| 6,124,523 A | 9/2000 | Banas et al. |
| 6,132,438 A | 10/2000 | Fleischman et al. |
| 6,152,144 A | 11/2000 | Lesh et al. |
| 6,165,196 A | 12/2000 | Stack et al. |
| 6,168,622 B1 | 1/2001 | Mazzocchi |
| 6,171,329 B1 | 1/2001 | Shaw et al. |
| 6,174,322 B1 | 1/2001 | Schneidt |
| 6,193,734 B1 | 2/2001 | Bolduc et al. |
| 6,206,907 B1 | 3/2001 | Marino et al. |
| 6,210,338 B1 | 4/2001 | Afremov et al. |
| 6,214,029 B1 | 4/2001 | Thill et al. |
| 6,231,561 B1 | 5/2001 | Frazier et al. |
| 6,241,678 B1 | 6/2001 | Afremov et al. |
| 6,245,012 B1 | 6/2001 | Kleshinski |
| 6,290,674 B1 | 9/2001 | Roue et al. |
| 6,325,815 B1 | 12/2001 | Kuslieka et al. |
| 6,334,864 B1 | 1/2002 | Amplatz et al. |
| 6,355,052 B1 | 3/2002 | Neuss et al. |
| 6,368,338 B1 | 4/2002 | Konya et al. |
| 6,368,339 B1 | 4/2002 | Amplatz |
| 6,371,971 B1 | 4/2002 | Tsugita et al. |
| 6,379,368 B1 | 4/2002 | Cororan et al. |
| 6,391,044 B1 | 5/2002 | Yadav et al. |
| 6,402,746 B1 | 6/2002 | Whayne et al. |
| 6,402,772 B1 | 6/2002 | Amplatz |
| 6,419,669 B1 | 7/2002 | Frazier et al. |
| 6,432,123 B2 | 8/2002 | Schwartz et al. |
| 6,436,088 B2 | 8/2002 | Frazier et al. |
| 6,440,152 B1 | 8/2002 | Gainor et al. |
| 6,447,531 B1 | 9/2002 | Amplatz |
| 6,458,100 B2 | 10/2002 | Roue et al. |
| 6,468,291 B2 | 10/2002 | Bates et al. |
| 6,468,301 B1 | 10/2002 | Amplatz et al. |
| D466,936 S | 12/2002 | Shaw et al. |
| 6,491,707 B2 | 12/2002 | Makower et al. |
| 6,506,204 B2 | 1/2003 | Mazzocchi |
| 6,508,828 B1 | 1/2003 | Akerfeldt |
| 6,511,496 B1 | 1/2003 | Huter et al. |
| 6,517,551 B1 * | 2/2003 | Driskill .................. 606/113 |
| 6,527,746 B1 | 3/2003 | Oslund et al. |
| 6,537,299 B1 | 3/2003 | Hogendijk et al. |
| 6,540,712 B1 | 4/2003 | Parodi et al. |
| 6,551,303 B1 | 4/2003 | Van Tassel et al. |
| 6,551,344 B2 | 4/2003 | Thill |
| 6,562,058 B2 | 5/2003 | Seguin et al. |
| 6,599,308 B2 | 7/2003 | Amplatz |
| 6,616,675 B1 | 9/2003 | Evard et al. |
| 6,623,508 B2 | 9/2003 | Shaw et al. |
| 6,641,557 B1 | 11/2003 | Frazier et al. |
| 6,650,923 B1 | 11/2003 | Lesh et al. |
| 6,652,555 B1 | 11/2003 | VanTassel et al. |
| 6,652,556 B1 | 11/2003 | VanTassel et al. |
| 6,656,206 B2 | 12/2003 | Corcoran et al. |
| 6,660,015 B1 | 12/2003 | Berg |
| 6,682,546 B2 | 1/2004 | Amplatz |
| 6,689,150 B1 | 2/2004 | VanTassel et al. |
| 6,712,804 B2 | 3/2004 | Roue et al. |
| 6,712,836 B1 | 3/2004 | Berg |
| 6,776,784 B2 | 8/2004 | Ginn |
| 6,860,895 B1 | 3/2005 | Akerfeldt et al. |
| 6,911,037 B2 | 6/2005 | Gainor et al. |
| 6,913,614 B2 | 7/2005 | Marino et al. |
| 7,338,514 B2 | 3/2008 | Wahr et al. |
| 2001/0000797 A1 | 5/2001 | Mazzocchi |
| 2001/0014800 A1 | 8/2001 | Frazier et al. |
| 2001/0021872 A1 | 9/2001 | Bailey et al. |
| 2001/0034537 A1 | 10/2001 | Shaw et al. |
| 2001/0037129 A1 | 11/2001 | Thill |
| 2001/0041914 A1 | 11/2001 | Frazier et al. |
| 2002/0022860 A1 | 2/2002 | Borillo et al. |
| 2002/0026094 A1 | 2/2002 | Roth |
| 2002/0029061 A1 | 3/2002 | Amplatz et al. |
| 2002/0035374 A1 | 3/2002 | Borillo et al. |
| 2002/0042625 A1 | 4/2002 | Stack et al. |
| 2002/0068950 A1 | 6/2002 | Corcoran et al. |
| 2002/0111647 A1 | 8/2002 | Khairkhahan et al. |
| 2002/0123759 A1 | 9/2002 | Amplatz |
| 2002/0123760 A1 | 9/2002 | Amplatz |
| 2002/0138094 A1 | 9/2002 | Borillo et al. |
| 2002/0138095 A1 | 9/2002 | Mazzocchi et al. |
| 2002/0138097 A1 | 9/2002 | Ostrovsky et al. |
| 2002/0161395 A1 | 10/2002 | Douk et al. |
| 2002/0169474 A1 | 11/2002 | Kusleika et al. |
| 2002/0169475 A1 | 11/2002 | Gainor et al. |
| 2002/0183787 A1 | 12/2002 | Wahr et al. |
| 2002/0198561 A1 | 12/2002 | Amplatz |
| 2002/0198563 A1 | 12/2002 | Gainor et al. |
| 2003/0023262 A1 | 1/2003 | Welch |
| 2003/0023266 A1 | 1/2003 | Borillo et al. |
| 2003/0028213 A1 | 2/2003 | Thill et al. |
| 2003/0045901 A1 | 3/2003 | Opolski |
| 2003/0057156 A1 | 3/2003 | Peterson et al. |
| 2003/0120337 A1 | 6/2003 | VanTassel et al. |
| 2003/0139819 A1 | 7/2003 | Beer et al. |
| 2003/0144694 A1 | 7/2003 | Chanduszko et al. |
| 2003/0181942 A1 | 9/2003 | Sutton et al. |
| 2003/0191495 A1 | 10/2003 | Ryan et al. |
| 2003/0191526 A1 | 10/2003 | Van Tassel et al. |
| 2003/0195530 A1 | 10/2003 | Thill |
| 2003/0195555 A1 | 10/2003 | Khairkhahan et al. |
| 2003/0199923 A1 | 10/2003 | Khairkhahan et al. |
| 2003/0204203 A1 | 10/2003 | Khairkhahan et al. |
| 2003/0212432 A1 | 11/2003 | Khairkhahan et al. |
| 2003/0225421 A1 | 12/2003 | Peavey et al. |
| 2004/0073242 A1 | 4/2004 | Chanduszko |
| 2004/0092973 A1 | 5/2004 | Chanduszko |
| 2004/0098047 A1 | 5/2004 | Frazier et al. |
| 2004/0098121 A1 | 5/2004 | Opolski |
| 2004/0133236 A1 | 7/2004 | Chanduszko |
| 2004/0143277 A1 | 7/2004 | Marino et al. |
| 2004/0143291 A1 | 7/2004 | Corcoran et al. |
| 2004/0143293 A1 | 7/2004 | Marino et al. |
| 2004/0143294 A1 | 7/2004 | Corcoran et al. |
| 2004/0162569 A1 | 8/2004 | Sikora et al. |
| 2004/0176799 A1 | 9/2004 | Chanduszko et al. |
| 2004/0186486 A1 | 9/2004 | Roue et al. |
| 2004/0193147 A1 | 9/2004 | Malecki |
| 2004/0215230 A1 | 10/2004 | Frazier et al. |
| 2004/0225324 A1 | 11/2004 | Marino et al. |
| 2004/0230185 A1 | 11/2004 | Malecki et al. |
| 2004/0267191 A1 | 12/2004 | Gifford, III et al. |
| 2005/0021016 A1 | 1/2005 | Malecki et al. |
| 2005/0033327 A1 | 2/2005 | Gainor et al. |
| 2005/0034735 A1 | 2/2005 | Deem et al. |
| 2005/0038470 A1 | 2/2005 | van der Burg et al. |
| 2005/0043711 A1 | 2/2005 | Corcoran et al. |
| 2005/0043759 A1 | 2/2005 | Chanduszko |
| 2005/0059983 A1 | 3/2005 | Opolski et al. |
| 2005/0065546 A1 | 3/2005 | Corcoran et al. |
| 2005/0065547 A1 | 3/2005 | Marino et al. |
| 2005/0065548 A1 | 3/2005 | Marino et al. |

| | | | |
|---|---|---|---|
| 2005/0080406 A1 | 4/2005 | Malecki et al. | |
| 2005/0090857 A1 | 4/2005 | Kusleika et al. | |
| 2005/0101984 A1 | 5/2005 | Chanduszko et al. | |
| 2005/0113861 A1 | 5/2005 | Corcoran et al. | |
| 2005/0113868 A1 | 5/2005 | Devellian et al. | |
| 2005/0119675 A1 | 6/2005 | Adams et al. | |
| 2005/0131401 A1 | 6/2005 | Malecki et al. | |
| 2005/0131460 A1 | 6/2005 | Gifford, III et al. | |
| 2005/0155612 A1 | 7/2005 | Matsuura et al. | |
| 2006/0009800 A1 | 1/2006 | Christianson et al. | |

FOREIGN PATENT DOCUMENTS

| | | |
|---|---|---|
| CA | 2057018 | 10/1991 |
| DE | 2822603 | 11/1979 |
| DE | 233303 A1 | 2/1986 |
| DE | 195 42 733 | 7/1997 |
| DE | 29713335 | 10/1997 |
| EP | 0 362 113 | 4/1990 |
| EP | 0539237 A1 | 4/1993 |
| EP | 0 541 063 | 5/1993 |
| EP | 0637454 A1 | 2/1995 |
| EP | 0680734 A2 | 11/1995 |
| EP | 0684022 A2 | 11/1995 |
| EP | 0701800 A1 | 3/1996 |
| EP | 0712614 A1 | 5/1996 |
| EP | 0732088 A2 | 9/1996 |
| EP | 0732089 A2 | 9/1996 |
| EP | 0807444 A2 | 11/1997 |
| EP | 1 175 867 | 1/2002 |
| EP | 1175867 A2 | 1/2002 |
| EP | 1281355 A2 | 2/2003 |
| EP | 1 013 227 | 8/2006 |
| FR | 2641692 | 1/1990 |
| GB | 489316 | 7/1938 |
| GB | 2269104 A | 2/1994 |
| WF | WO 01/87163 A1 | 11/2001 |
| WO | WO 89/08433 A1 | 9/1989 |
| WO | WO 91/05088 | 4/1991 |
| WO | WO 93/00868 A1 | 1/1993 |
| WO | WO 93/13712 | 7/1993 |
| WO | WO 93/20757 A2 | 10/1993 |
| WO | WO 94/01056 A1 | 1/1994 |
| WO | WO 95/21592 A1 | 8/1995 |
| WO | WO 95/26695 | 10/1995 |
| WO | WO 95/28885 | 11/1995 |
| WO | WO 95/32757 A1 | 12/1995 |
| WO | WO 96/01591 A1 | 1/1996 |
| WO | WO 96/01599 A1 | 1/1996 |
| WO | WO 96/14808 A1 | 5/1996 |
| WO | WO 96/18361 A1 | 6/1996 |
| WO | WO 96/22745 A1 | 8/1996 |
| WO | WO 96/25897 A2 | 8/1996 |
| WO | WO 96/40356 | 12/1996 |
| WO | WO 97/13463 A1 | 4/1997 |
| WO | WO 97/13471 A1 | 4/1997 |
| WO | WO 97/27898 A1 | 8/1997 |
| WO | WO 97/41779 | 11/1997 |
| WO | WO 97/42878 | 11/1997 |
| WO | WO 98/01086 | 1/1998 |
| WO | WO 98/02099 A1 | 1/1998 |
| WO | WO 98/03118 A1 | 1/1998 |
| WO | 9807399 | 2/1998 |
| WO | WO 98/08462 | 3/1998 |
| WO | WO 98/09671 | 3/1998 |
| WO | 9816161 | 4/1998 |
| WO | WO 98/19629 A2 | 5/1998 |
| WO | WO 98/19631 | 5/1998 |
| WO | WO 98/26732 | 6/1998 |
| WO | WO 98/27868 | 7/1998 |
| WO | WO 98/27894 | 7/1998 |
| WO | WO 98/19629 A3 | 9/1998 |
| WO | WO 98/38939 A1 | 9/1998 |
| WO | WO 98/38941 A1 | 9/1998 |
| WO | WO 98/38942 A1 | 9/1998 |
| WO | WO 98/42262 | 10/1998 |
| WO | WO 98/55027 A2 | 12/1998 |
| WO | WO 99/07289 | 2/1999 |
| WO | WO 99/17816 | 4/1999 |
| WO | WO 99/38454 | 5/1999 |
| WO | WO 99/39646 | 8/1999 |
| WO | WO 99/62408 A1 | 12/1999 |
| WO | WO 00/10452 | 3/2000 |
| WO | WO 00/12012 | 3/2000 |
| WO | WO 00/16705 | 3/2000 |
| WO | WO 00/27292 | 5/2000 |
| WO | WO 00/56245 | 9/2000 |
| WO | WO 01/15629 A1 | 3/2001 |
| WO | WO 01/17435 A1 | 3/2001 |
| WO | WO 01/30266 A1 | 5/2001 |
| WO | WO 01/30267 A1 | 5/2001 |
| WO | WO 01/30268 A1 | 5/2001 |
| WO | WO 01/72367 A1 | 10/2001 |
| WO | WO 01/91844 A1 | 12/2001 |
| WO | WO 02/15793 A2 | 2/2002 |
| WO | WO 02/24106 A2 | 3/2002 |
| WO | WO 02/098298 | 12/2002 |
| WO | WO 03/009880 A2 | 2/2003 |
| WO | WO 03/053493 A3 | 7/2003 |
| WO | WO 03/059152 A2 | 7/2003 |
| WO | WO 03/082076 A2 | 10/2003 |
| WO | WO 03/103476 A2 | 12/2003 |
| WO | WO 2005/006990 A2 | 1/2005 |
| WO | WO 2005/027752 A1 | 3/2005 |
| WO | WO 2005/039419 A1 | 5/2005 |

OTHER PUBLICATIONS

U.U. Babic, MD, "Experience with ASDOS for Transcatheter Closure of Atrial Septal Defect and Patent Foramen Ovale," *Current Interventional Cardiology Reports*, 2:177-183, 2000).

Terry King et al., "Secundum Atrial Septal Defect," *JAMA*, vol. 235, No. 23, pp. 2506-2509, Jun. 1976.

Makram R. Ebeid, MD, "Percutaneous Catheter Closure of Secundum Atrial Septal Defects: A Review," *J. Invas. Cardiol.* 2002; 14: 25-31.

Brochure and Instructions for Use for "CardioSeal® Septal Occlusion System," An Alternative FDA Approved Solution for Patients Needing Closure of Ventricular Septal Defects, NMT Medical Inc., 1999, pp. 1-24.

U.S. Appl. No. 10/411,152, filed Apr. 11, 2003.
U.S. Appl. No. 11/522,157, filed Sep. 16, 2006.
U.S. Appl. No. 11/522,158, filed Sep. 16, 2006.
U.S. Appl. No. 11/522,193, filed Sep. 16, 2006.

* cited by examiner

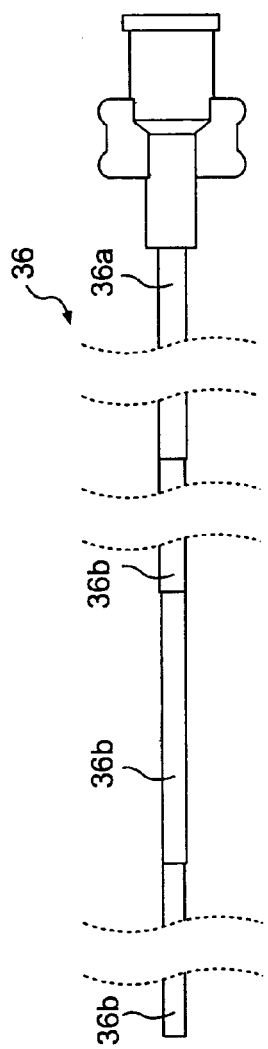
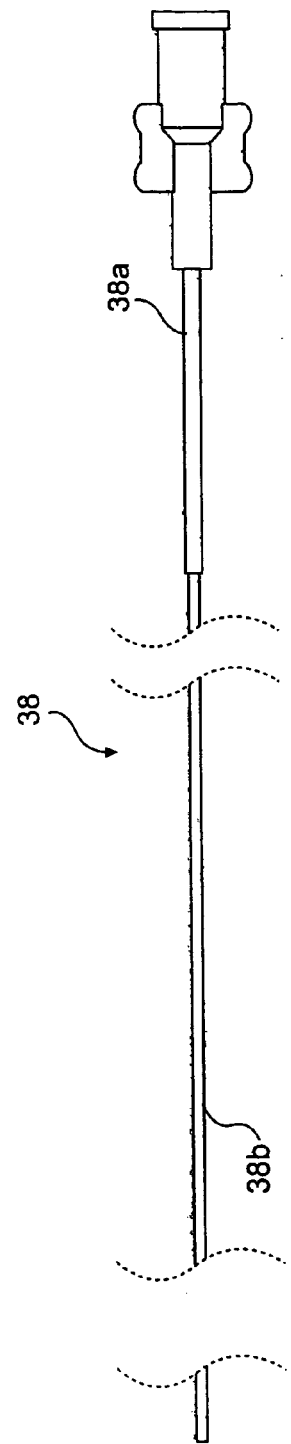
FIG. 17
FIG. 18

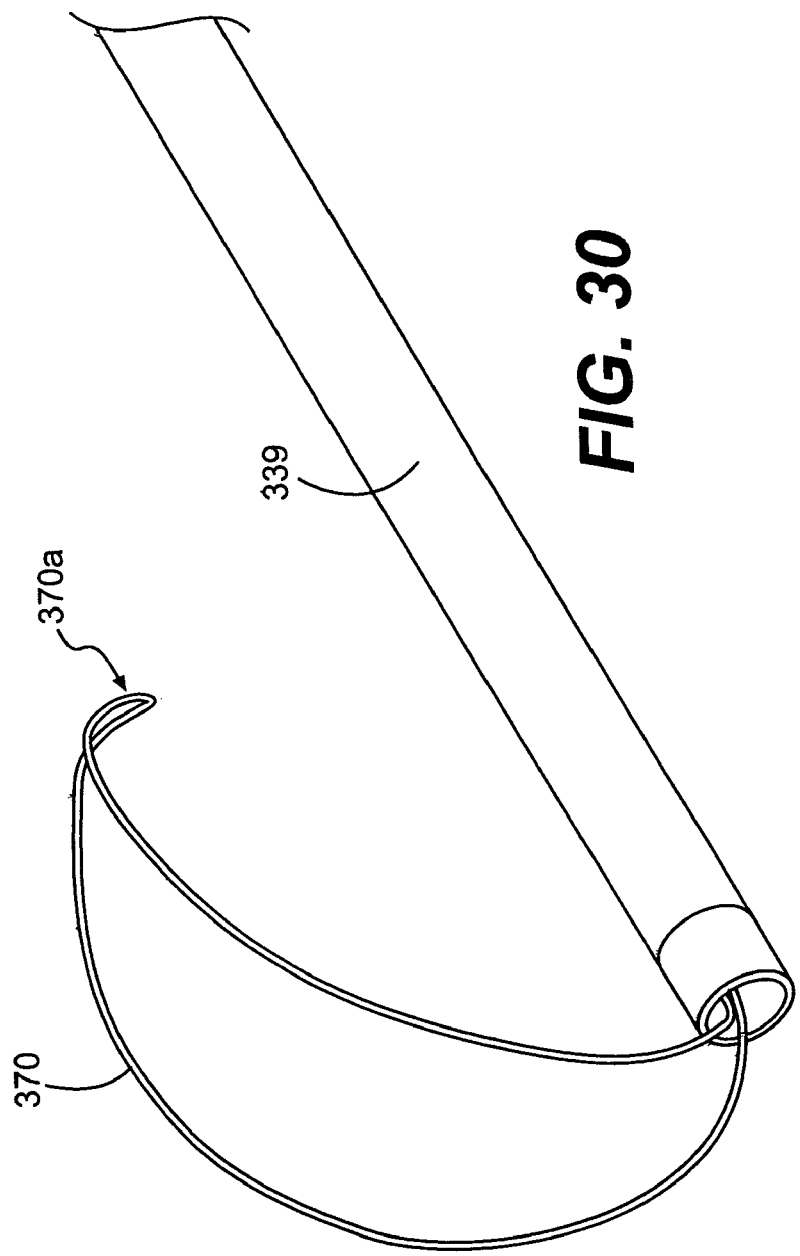

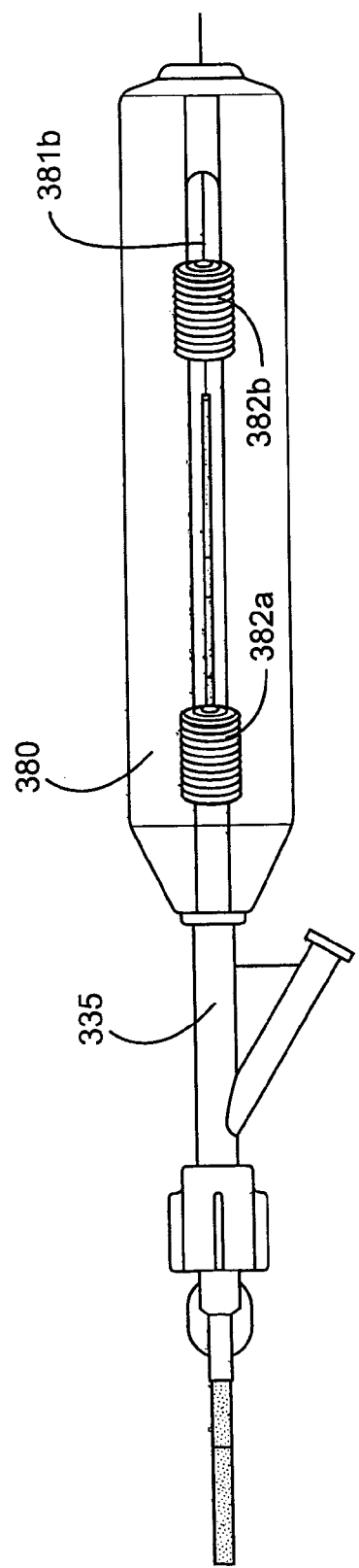

CLOSURE DEVICES, RELATED DELIVERY METHODS, AND RELATED METHODS OF USE

RELATED APPLICATIONS

This application is a continuation-in-part of U.S. patent application Ser. No. 10/411,152, filed on Apr. 11, 2003, and entitled "Closure Devices, Related Delivery Methods, and Related Methods of Use," now abandoned, the entire disclosure of which is incorporated herein by reference.

FIELD OF THE INVENTION

This invention relates to devices for closing a passageway in a body, for example a patent foramen ovale in a heart, related methods and devices for delivering such closure devices, and related methods of using such closure devices for sealing the passageway.

BACKGROUND OF THE INVENTION

FIG. 1 shows a portion of a heart in longitudinal section, with the right atrium (RA), left atrium (LA), right ventricle (RV) and left ventricle (LV) shown. FIG. 1 also shows the septum primum (SP), a flap-like structure, which normally covers the foramen ovale, an opening in the septum secundum (SS) of the heart. In utero, the foramen ovale serves as a physiologic conduit for right-to-left shunting of blood in the fetal heart. After birth, with the establishment of pulmonary circulation, the increased left atrial blood flow and pressure presses the septum primum (SP) against the walls of the septum secundum (SS), covering the foramen ovale and resulting in functional closure of the foramen ovale. This closure is usually followed by anatomical closure of the foramen ovale due to fusion of the septum primum (SP) to the septum secundum (SS).

Where anatomical closure of the foramen ovale does not occur, a patent foramen ovale (PFO) is created. A patent foramen ovale is a persistent, usually flap-like opening between the atrial septum primum (SP) and septum secundum (SS) of a heart. A patent foramen ovale results when either partial or no fusion of the septum primum (SP) to the septum secundum (SS) occurs. In the case of partial fusion, a persistent passageway exists between the superior portion of the septum primum (SP) and septum secundum (SS). It is also possible that more than one passageway may exist between the septum primum (SP) and the septum secundum (SS).

Studies have shown that a relatively large percentage of adults have a patent foramen ovale (PFO). It is believed that embolism via a PFO may be a cause of a significant number of ischemic strokes, particularly in relatively young patients. It has been estimated that in 50% of cryptogenic strokes, a PFO is present. Patients suffering a cryptogenic stroke or a transient ischemic attack (TIA) in the presence of a PFO often are considered for medical therapy to reduce the risk of a recurrent embolic event.

Pharmacological therapy often includes oral anticoagulants or antiplatelet agents. These therapies may lead to certain side effects, including hemorrhaging. If pharmacologic therapy is unsuitable, open heart surgery may be employed to close a PFO with stitches, for example. Like other open surgical treatments, this surgery is highly invasive, risky, requires general anesthesia, and may result in lengthy recuperation.

Nonsurgical closure of PFOs is possible with umbrella-like devices developed for percutaneous closure of atrial septal defects (ASD) (a condition where there is not a septum primum (SP)). Many of these conventional devices used for ASDs, however, are technically complex, bulky, and difficult to deploy in a precise location. In addition, such devices may be difficult or impossible to retrieve and/or reposition should initial positioning not be satisfactory. Moreover, these devices are specially designed for ASDs and therefore may not be suitable to close and seal a PFO, particularly because the septum primum (SP) overlaps the septum secundum (SS).

SUMMARY OF THE INVENTION

In accordance with the invention, methods, tools, and devices for closing a passageway in a body, and more specifically closing a patent foramen ovale (PFO), are provided.

According to one aspect of the invention, an assembly for sealing a passageway in a heart is provided. The assembly comprises a closure device for sealing a passageway in a heart including a first anchor adapted to be placed proximate a first end of the passageway, a second anchor adapted to be placed proximate a second end of the passageway, and a flexible elongate member adapted to extend through the passageway and connect the first and second anchors, the second anchor capable of movement relative to the elongate flexible member to vary a length of the elongate member between the first and second anchors, and a delivery system for delivering the closure device to the passageway in the heart, the delivery system being configured to move within a lumen of a guide catheter and including a wire configured to control movement of the second anchor along the flexible elongate member.

According to another aspect of the invention, a method of sealing a passageway in a heart is provided. The method comprises advancing a first anchor out of a lumen of a guide catheter, placing the first anchor proximate a first end of the passageway, advancing a second anchor out of the lumen of the guide catheter, controlling movement of the second anchor relative to the first anchor along a flexible elongate member disposed between the first and second anchors, wherein controlling movement of the second anchor includes varying a distance between the first and second anchors, and placing the second anchor proximate a second end of the passageway.

According to a further aspect of the present invention, a method of retrieving a closure device misdeployed in a chamber in a heart is provided. The method comprises advancing a retrieval device through a lumen of a guide catheter and into the chamber of the heart containing a closure device having first and second anchors and a flexible member connecting the first and second anchors, expanding a retrieval portion of the retrieval device from a collapsed configuration to an expanded configuration, moving the first and second anchors of the closure device into the retrieval portion, moving the retrieval portion and the closure device within the retrieval portion toward the guide catheter, collapsing the retrieval portion and the closure device within the retrieval portion, and withdrawing the collapsed retrieval portion and closure device from the chamber into the guide catheter.

According to yet another aspect of the present invention, a retrieval device configured to capture and remove an implantable device from an area in the human body is provided. The retrieval device comprises a proximal shaft portion, and a distal retrieval portion connected to the proximal shaft portion and configured to enclose and contain an implantable device within an area of the human body, wherein the retrieval portion is movable between a collapsed configuration and an expanded configuration, and wherein the retrieval portion is configured to move through a lumen of a guide catheter in the collapsed configuration and is configured to expand upon exiting the lumen of the guide catheter.

According to one aspect of the invention, a device for sealing a passageway in a human body is provided. The device comprises a first anchor adapted to be placed proximate a first end of the passageway, the first anchor including a plurality of first loop structures, each first loop structure having a first end connected to the first anchor and a second free end, a second anchor adapted to be placed proximate a second end of the passageway, and an elongate member adapted to extend through the passageway and connect the first and second anchors, the elongate member having a first end fixedly connected to one of the first and second anchors.

According to another aspect of the invention, a device for sealing a passageway in a human body comprises a first anchor adapted to be placed proximate a first end of the passageway, the first anchor including a plurality of first loop structures, each first loop structure having a first end connected to the first anchor and a second free end, a second anchor adapted to be placed proximate a second end of the passageway, and a flexible elongate member adapted to extend through the passageway and connect the first and second anchors, the elongate member capable of moving through the second anchor to vary a length of the elongate member between the first and second anchors.

According to a further aspect of the invention, the device for sealing a passageway in a human body comprises a first anchor adapted to be placed proximate a first end of the passageway, the first anchor including a plurality of first loop structures, each first loop structure having a first end connected to the first anchor and a second free end, a second anchor adapted to be placed proximate a second end of the passageway, the second anchor including a plurality of second loop structures, and a flexible elongate member adapted to extend through the passageway and connect the first and second anchors, the elongate member capable of moving through the second anchor to vary a length of the elongate member between the first and second anchors.

According to yet another aspect of the invention, a device for sealing a passageway in a human body comprises a first anchor adapted to be placed proximate a first end of the passageway, the first anchor including a plurality of first loop structures, each first loop structure having a first end connected to the first anchor and a second free end, a second anchor adapted to be placed proximate a second end of the passageway, and a flexible elongate member adapted to extend through the passageway and connect the first and second anchors, wherein the first anchor pivots relative to the elongate member and the second anchor pivots relative to the elongate member.

According to another aspect of the present invention, a device for sealing a passageway in a human body comprises a first anchor adapted to be placed proximate a first end of the passageway, the first anchor including a plurality of first loop structures, each first loop structure having a first end connected to the first anchor and a second free end, a second anchor adapted to be placed proximate a second end of the passageway, and a flexible elongate member adapted to extend through the passageway and connect the first and second anchors, wherein each of the first and second anchors is collapsible from a deployed state to a collapsed delivery state.

According to a further aspect of the present invention, a device for sealing a passageway in a human body comprises a first anchor adapted to be placed proximate a first end of the passageway, the first anchor including a plurality of first loop structures, each loop structure including an outer loop portion and a member connecting portions of outer loop portion, a second anchor adapted to be placed proximate a second end of the passageway, and an elongate member adapted to extend through the passageway and connect the first and second anchors, the elongate member having a first end fixedly connected to the first anchor.

According to yet another aspect of the invention, an assembly for sealing a passageway in a heart is provided. The assembly comprises a guide catheter capable of extending to the passageway, and a closure device capable of sealing the passageway, the closure device including a first anchor adapted to be placed proximate a first end of the passageway, the first anchor including a plurality of first loop structures, each first loop structure having a first end connected to the first anchor and a second free end, a second anchor adapted to be placed proximate a second end of the passageway, and a flexible elongate member adapted to extend through the passageway and connect the first and second anchors, wherein the closure device is positionable within the guide catheter in a first collapsed state and extendable from the guide catheter in a second deployed state.

According to another aspect of the invention, a method of sealing a passageway in a human body is provided. The method comprises placing a first anchor proximate a first end of the passageway, the first anchor including a plurality of first loop structures, placing a second anchor proximate a second end of the passageway, and moving the second anchor relative to the first anchor along a flexible elongate member disposed between the first and second anchors within the passageway.

According to a further aspect of the invention, a method of placing a closure device to seal a passageway in a human body is provided. The method comprises advancing a catheter into a first end of the passageway and out a second end of the passageway, advancing a first anchor of a closure device out of a distal end of the catheter, withdrawing the catheter through the passageway, positioning the first anchor adjacent the second end of the passageway, advancing a second anchor of the closure device out of the distal end of the catheter, positioning the second anchor of the closure device adjacent the first end of the passageway, and advancing a lock to a position adjacent the second anchor.

According to yet another aspect of the invention, a closure device for sealing a passageway in a heart is provided. The closure device comprises a left atrial anchor configured to close a first end of the passageway, a right atrial anchor configured to close a second end of the passageway, at least one of the left atrial anchor and the right atrial anchor including a plurality of loop structures, a flexible elongate member connecting the left and right atrial anchors, wherein the elongate member has a first end fixedly connected to the left atrial anchor and wherein the right atrial anchor is movable with respect to the elongate member, and a lock configured to prevent proximal movement of the right atrial anchor relative to the flexible elongate member.

According to another aspect of the invention, a system for sealing a passage in a heart is provided. The system comprises a delivery catheter capable of extending to a position near the passage, a closure device capable of sealing the passage, the device including a first anchor adapted to be placed proximate a first end of the passage, a second anchor adapted to be placed proximate a second end of the passage, and a flexible elongate member adapted to extend through the passage and connect the first and second anchors, and a cutting tool capable of extending over the flexible elongate member to a position near the second anchor.

According to yet another aspect of the invention, a device for sealing a passageway in a human body is provided. The device comprises a first anchor adapted to be placed proximate a first end of the passageway, the first anchor including a plurality of first loop structures, each loop structure having a first end connected to the first anchor and a second free end, a second anchor adapted to be placed proximate a second end of the passageway, the second anchor including an element configured to engage a snare, and a flexible elongate member connecting the first and second anchors.

According to another aspect of the invention, a device for closing a passageway in a heart comprises a left atrial anchor adapted to be placed in a left atrium of the heart and including a plurality of uncovered arms, a right atrial anchor adapted to be placed in a right atrium of the heart and including a plurality of arms, a cover attached to the plurality of arms, and an element configured to engage a snare, and a flexible elongate member adapted to extend through the passageway and connect the left and right atrial anchors, the elongate member having a first end fixedly connected to the left atrial anchor and a second end releasably connected to the right atrial anchor.

According to yet another aspect of the invention, a device for closing a passageway in a heart comprises a left atrial anchor adapted to be placed in a left atrium of the heart and including a plurality of uncovered arms, a right atrial anchor adapted to be placed in a right atrium of the heart and including a plurality of arms and a cover attached to the plurality of arms, a flexible elongate member adapted to extend through the passageway and connect the left and right atrial anchors, the elongate member having a first end fixedly connected to the left atrial anchor, and a lock for preventing proximal movement of the right atrial anchor relative to the flexible elongate member.

According to another aspect of the invention, a device for closing a passageway in a heart comprises a left atrial anchor adapted to be placed in a left atrium of the heart and including a plurality of uncovered arms and at least one member connecting each arm to the left atrial anchor, a right atrial anchor adapted to be placed in a right atrium of the heart and including a plurality of arms and a cover attached to the plurality of arms, and a flexible elongate member adapted to extend through the passageway and connect the left and right atrial anchors, the elongate member having a first end fixedly connected to the left atrial anchor and a second end releasably connected to the right atrial anchor.

According to a further aspect of the invention, a method for retrieving a device for sealing a passageway in a heart is provided. The method comprises advancing a snare catheter through a guide catheter toward the passageway covered by a second anchor of the device, engaging a portion of the second anchor with the snare, and drawing the second anchor into the guide catheter with the snare.

According to yet another aspect of the invention, a cutting tool for severing a flexible elongate member is provided. The cutting tool comprises a cutting tool body having a distal end and a proximal end, the cutting tool body capable of extending through a guide catheter, a guide member for guiding the flexible elongate member, the guide member including a distal opening through which the flexible elongate member enters the cutting tool and a lateral opening through which the flexible elongate member exits the cutting tool, and a cutting element surrounding the guide member, wherein the cutting element is movable relative to the guide member to cut the flexible elongate member as it exits the guide member through the lateral opening of the guide member.

Additional advantages of the invention will be set forth in part in the description which follows, and in part will be obvious from the description, or may be learned by practice of the invention. The objects and advantages of the invention will be realized and attained by means of the elements and combinations particularly pointed out in the appended claims.

The foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the invention and together with the description, serve to explain the principles of the invention.

FIG. 17 is a side view of an outer tube of the delivery catheter, according to an embodiment of the present invention;

FIG. 18 is a side view of an inner tube of the delivery catheter, according to an embodiment of the present invention;

FIG. 30 is an isometric view of a release wire tube of a delivery system with a release wire extending therefrom, according to one aspect of the present invention;

FIG. 31c is a top view of the handle of FIG. 31a after release of a release wire, according to one aspect of the present invention.

DESCRIPTION OF THE EMBODIMENTS

Reference will now be made in detail to embodiments of the invention, examples of which are illustrated in the accompanying drawings. Wherever possible, the same reference numbers will be used throughout the drawings to refer to the same or like parts.

The various Figures show embodiments of patent foramen ovale (PFO) closure devices, devices and methods for delivery of the PFO closure devices, and methods of using the device to close a PFO. The devices and related methods are described herein in connection with use in sealing a PFO. These devices, however, also are suitable for closing other openings or passageways, including other such openings in the heart, for example atrial septal defects, ventricular septal defects, and patent ductus arterioses, and openings or passageways in other portions of a body such as an arteriovenous fistula. The invention therefore is not limited to use of the inventive closure devices to close PFOs.

Figure 1:
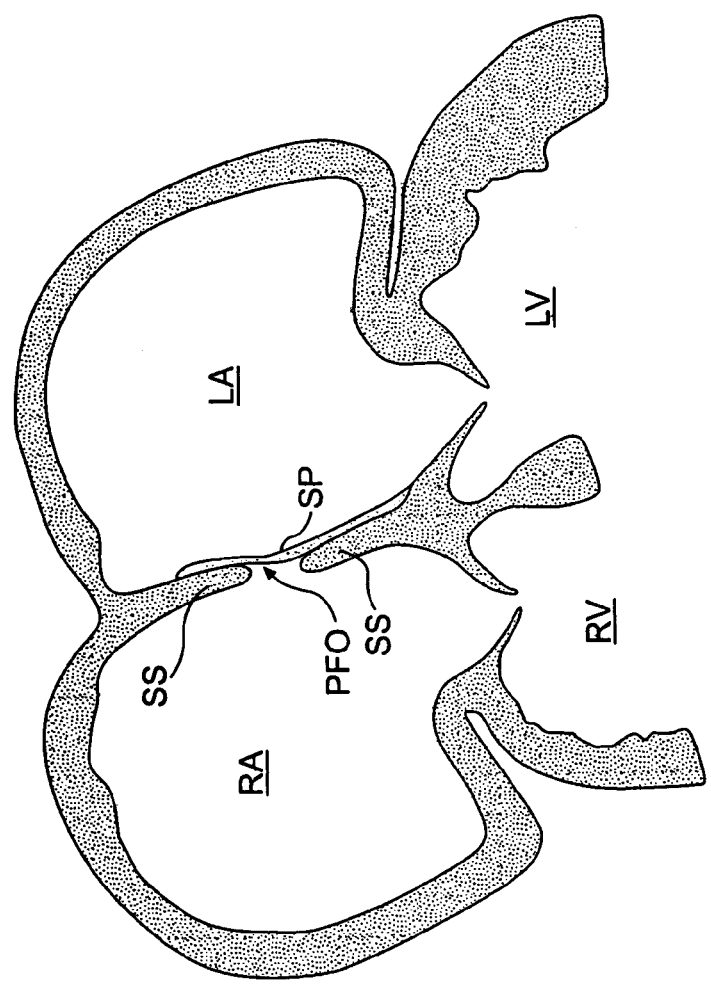
FIG. 1 is a longitudinal section of a portion of a heart having a PFO.
Figure 2:
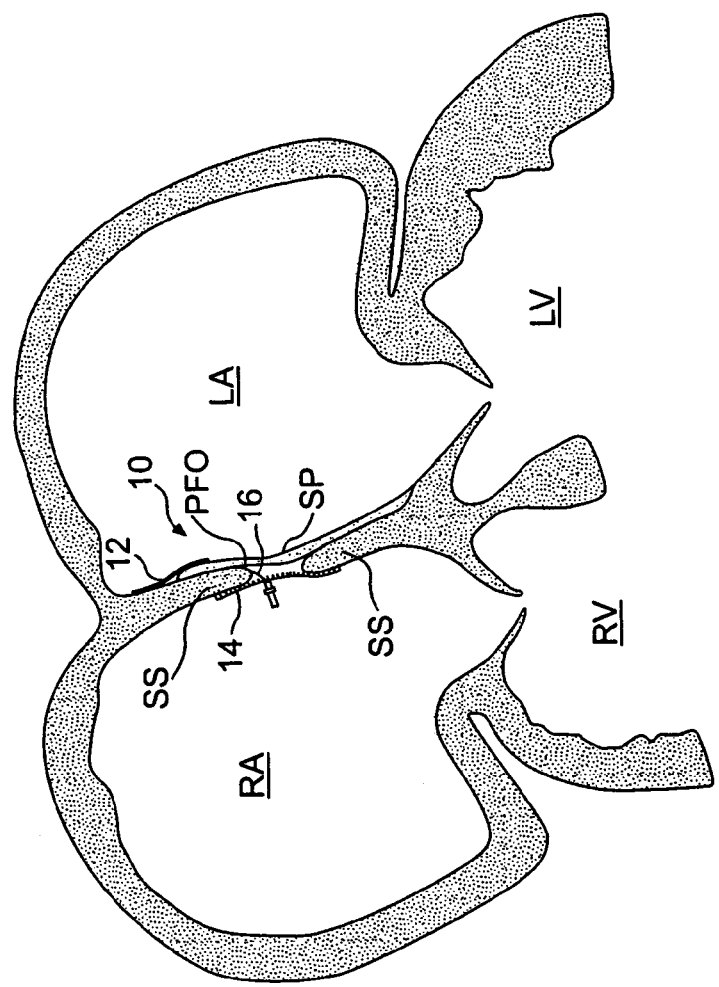
FIG. 2 is a closure device positioned in a heart to close a PFO, according to an embodiment of the present invention.
Figure 12:
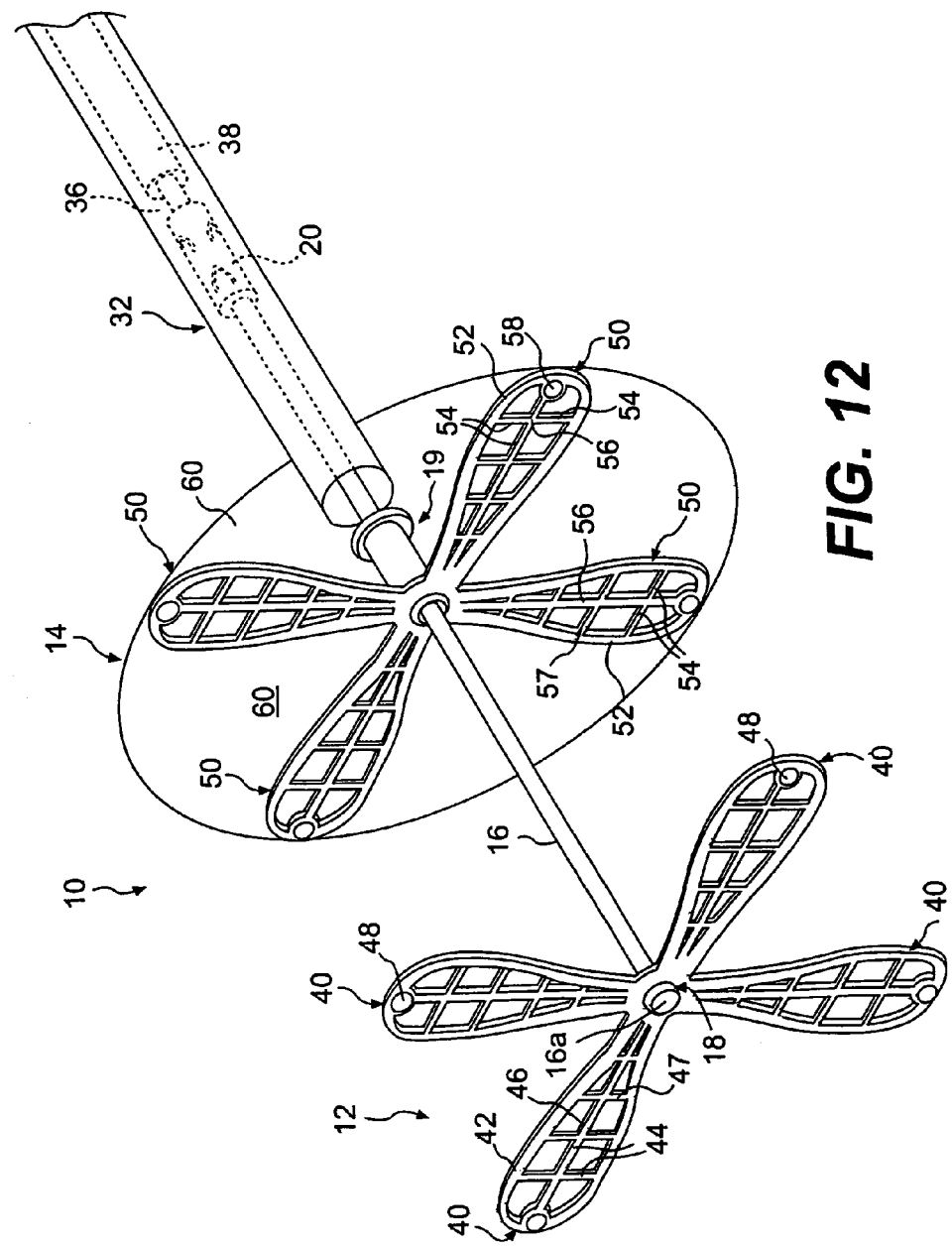
FIG. 12 is an isometric view of a closure device extending from a delivery catheter, according to one aspect of the invention.
Figure 15:
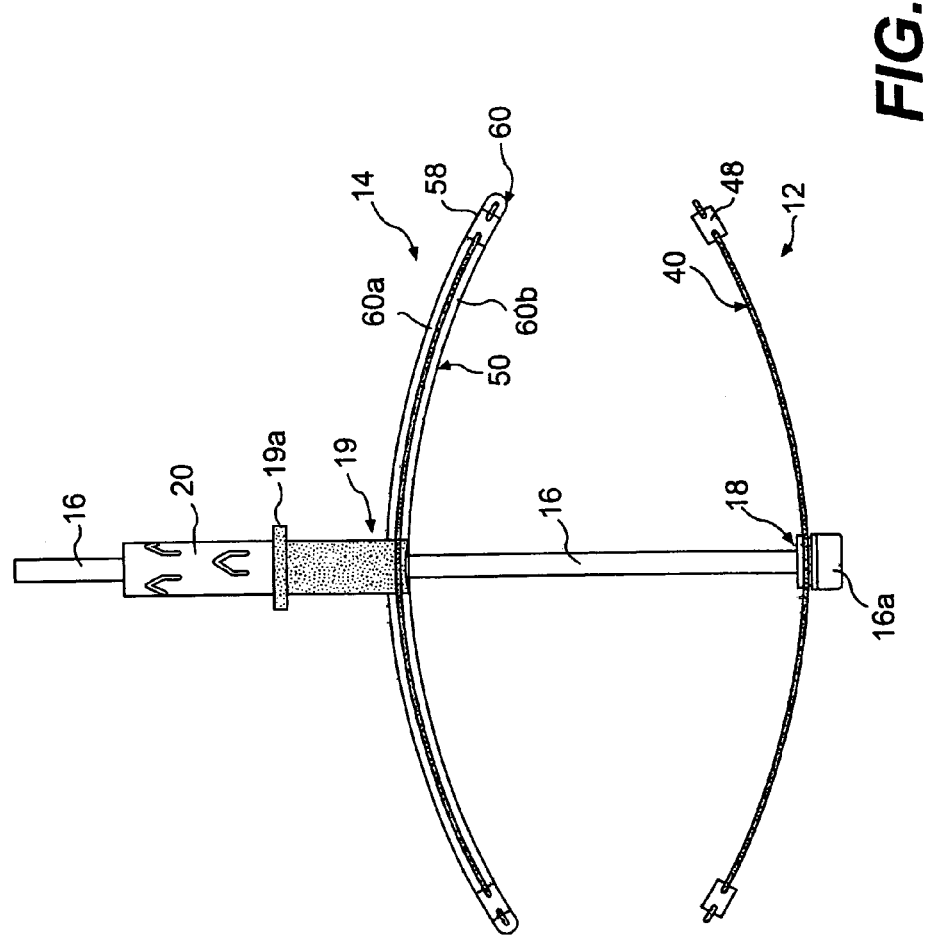
FIG. 15 is a cross-sectional side view of the closure device of FIG. 12 with a lock, according to an embodiment of the present invention.

FIGS. 2, 12, and 15 show a PFO closure device 10 according to an embodiment of the present invention. In FIG. 2, device 10 is shown positioned on either side of a PFO track (referenced as PFO in the Figures) with a portion of the device 10 passing through the PFO track, after delivery from a delivery system. The PFO track can be seen more clearly in FIG. 3, which shows a catheter disposed in the PFO track between the septum primum (SP) and septum secundum (SS). As shown in FIG. 2, closure device 10 includes a left atrial anchor 12 positioned in the LA, a right atrial anchor 14 positioned in the RA, and a tether 16 connecting the anchor structures.

As embodied herein and shown in FIGS. 2, 12, and 15, a PFO closure device 10 includes a left atrial anchor 12, a right atrial anchor 14, a tether 16, and a lock 20. FIG. 12 shows left atrial anchor 12 and right atrial anchor 14 schematically in a deployed condition. As shown in FIGS. 12 and 15, left atrial anchor 12 is permanently secured to the distal end 16a of the tether 16 via a hub 18. Hub 18 is preferably tubular in shape such that tether 16 extends through hub 18 to right atrial anchor 14. Right atrial anchor 14 is slidably disposed about the tether 16 via a second tubular hub 19. Lock 20 is advanceable along the tether 16, in a distal direction only, to secure the right atrial anchor 14 in position against the atrial tissue defining the PFO track. Tether 16 will be severed adjacent to lock 20; and left atrial anchor 12, right atrial anchor 14 connected to left atrial anchor 12 via tether 16, and lock 20 will remain in the heart to seal the PFO.

Figure 13:
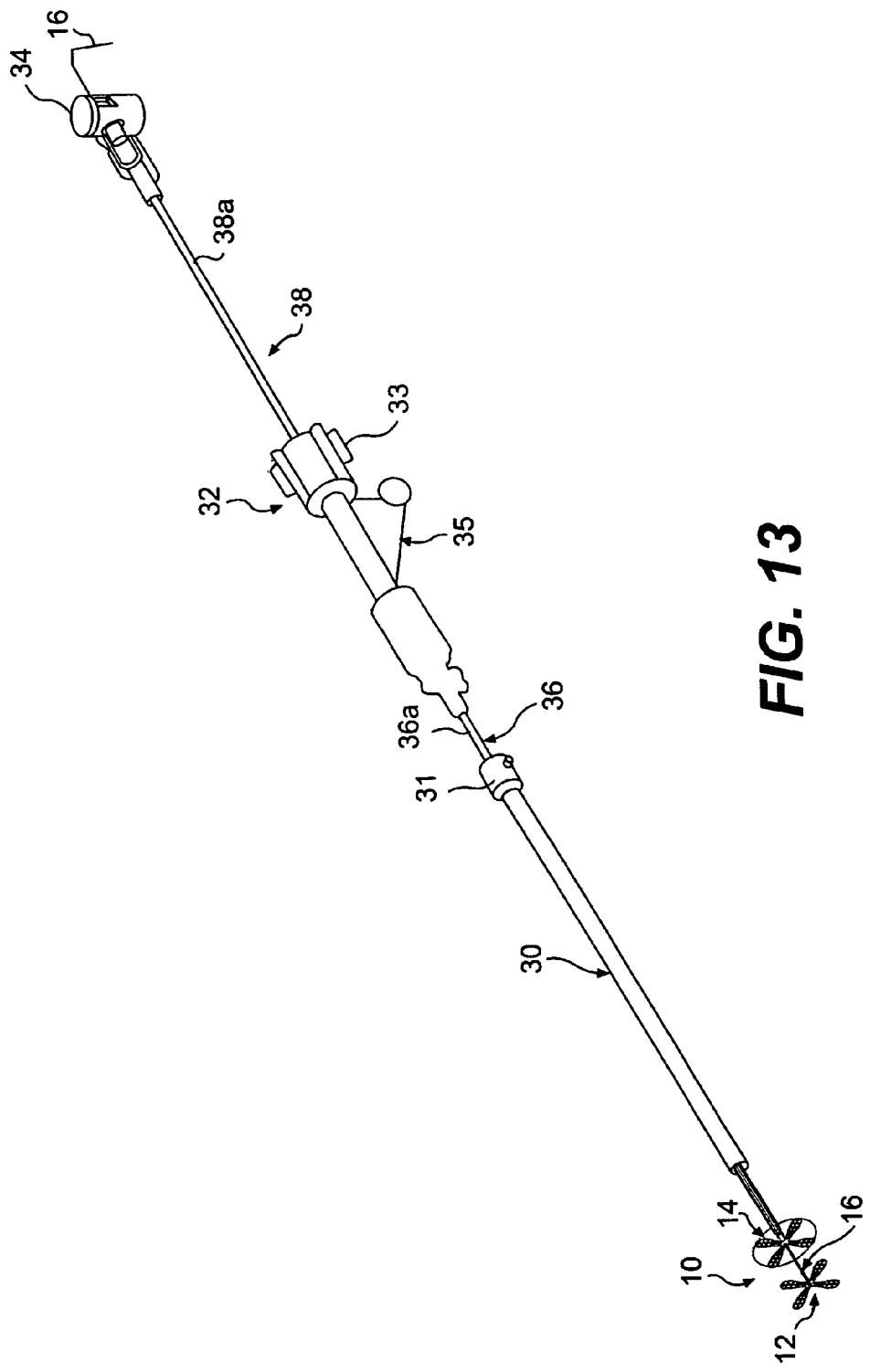
FIG. 13 is an isometric view of the closure device of FIG. 12, with a delivery catheter, and a guide catheter, according to an embodiment of the present invention.

As shown in FIG. 13, the tether 16 extends through the right atrial anchor 14, through a delivery catheter 32 (that passes through a lumen of a guide catheter 30), and emerges from the proximal end of the delivery catheter 32. An adjustable tether clip 34 provides for temporary securement of the tether 16 relative to the delivery catheter 32. The tether clip 34 may be, for example, a spring-loaded clamp similar to those used to secure laces and drawstrings on backpacks or camping and other equipment.

The tether 16 is preferably a high strength flexible polymeric material, such as a braid of polyester yarn. Preferably, such a braided yarn is approximately 0.010 to 0.025 inch in diameter, and most preferably is about 0.0175 inch. Suitable materials include, but are not limited to, multifilament yarns of ultra-high molecular weight polyethylene (UHMWPE) such as SPECTRA™ or DYNEEMA™. Other suitable materials include liquid crystal polymer (LCP) such as VECTRAN™, polyester, or other high strength fibers. Alternatively, the tether 16 could be formed of a high strength polymeric monofilament. The distal end of the tether 16 may be frayed and encapsulated with an adhesive to form a ball shape, which mechanically engages the hub 18, permanently connecting the distal end of the tether 16 to the left atrial anchor 12. Alternatively, the distal end of the tether 16 could be knotted and trimmed to yield a ball shape for engagement with hub 18 of left atrial anchor 12. FIGS. 12 and 15 illustrate an embodiment of left atrial anchor 12 and its connection to tether 16.

As embodied herein and shown in FIGS. 12 and 15, left atrial anchor 12 includes one or more arms 40, which extend radially outward from hub 18. As shown, a left atrial anchor 12 preferably includes four arms 40, although fewer or more arms may be provided. Arms 40 preferably form a unitary arm structure, such that the arms are connected to each other around hub 18. Each arm 40 is preferably ovoid in shape to prevent tissue trauma. The primary structural element of the arm 40 is a loop 42, which extends from near the center of the unitary arm structure and hub 18, towards the periphery of the left atrial anchor 12, and loops back towards the hub 18. The outer portion of the loop 42 defines an atraumatic curve. As shown in FIGS. 12 and 15, each arm 40 includes a first end connected to the hub 18 and/or other arms 40 and a second free end formed by the outer portion of the loop 42. At least the portion of each arm 40 that is unconnected to the other arms 40 of the unitary arm structure is freely movable, i.e., it is movable independently from the other arms 40.

The unitary arm structure, including the arms 40, is preferably formed from a rolled sheet of binary nickel titanium alloy (also known as nitinol). The alloy is known in the art to have superior elastic properties. The geometry of the unitary arm structure may be formed either by laser cutting or chemical etching. A smooth and passive surface is created by electropolishing. Thermal processing is used to impart a parent shape, as is known in the art. A preferred parent shape is shown in FIG. 15. This curved shape (shown in side view) for the left atrial anchor 12 presents a concave surface to the left atrial wall.

The arms 40, as shown in FIG. 12, may incorporate an optional web 44. The web 44 includes one or more radial struts 46, intersected by cross struts 47. The web 44 is preferably thinner in dimension than the loop 42. As such, the web 44 adds relatively little to the stiffness of the arm, but adds redundancy to the arm in the event of a fracture in the loop 42. Since the web 44 is thinner, any oscillating motion (primarily perpendicular to the surface of the arm) imparted to the arms 40 due to the beating of the heart will cause an oscillatory strain on the loop 42. Such a strain will be greatest near the hub 18. However, the strain imparted to the web 44 will be significantly less than that imparted to the loop 42, due to the thinness of the web 44. Thus, in the event of a fracture in the loop 42, the web 44 will maintain a connection between the arm 40 and the remainder of the unitary arm structure forming the left atrial anchor 12.

The diameter (span) of the left atrial anchor 12 is primarily determined by the size of the unitary arm structure. In a PFO closure application, the span of the unitary arm structure is preferably from about 10 mm to about 40 mm, and is most preferably from about 15 mm to about 25 mm. The preferred span width of the entire loop 42 at its widest point is preferably from about 0.050 inch to about 0.150 inch, and is most preferably about 0.100 inch. The rolled sheet that forms the loop 42 is preferably between about 0.003 inch and about 0.006 inch uniform thickness, and is most preferably about 0.045 inch, with a width of the loop 42 between about 0.002 inch and about 0.015 inch. The loop 42 is preferably wider near the hub 18, and narrower further away. The struts 46, 47 of the web 44 are thinner than the material forming the loop 42, preferably between about 0.001 inch and about 0.004 inch in width and thickness. The only structure within the left atrium is the relatively small struts of the arms 40, which are preferably well apposed to the wall tissue by virtue of their imparted parent shape. These small struts will readily be incorporated into the tissue of the left atrium, resulting in an endothelialized non-thrombogenic surface.

At the center of the unitary arm structure forming the left atrial anchor 12 is a hole, through which the hub 18 is secured. The hub 18 is preferably a tube formed of radiopaque material such as platinum alloy, and is swaged in place, forming a mechanical interlock with the unitary arm structure that forms left atrial anchor 12. The hub 18 serves to engage the distal bulb 16*a* of the tether 16, as previously described.

To facilitate visualization during and following implantation of the PFO closure device 10, markers 48 are provided on the arms 40. Holes near the free ends of the arms 40 are formed into the geometry of the unitary arm structure. Markers 48 may include, for example, rivets formed from a radiopaque material such as platinum alloy. The markers 48 are positioned into the holes and swaged in place.

FIGS. 12 and 15 also illustrate an embodiment of right atrial anchor 14. As embodied herein and shown in FIGS. 12 and 15, right atrial anchor 14 includes arms 50, which extend radially outward from hub 19. The structure of each arm 50 is essentially identical to that described for left atrial anchor 12. As shown in FIGS. 12 and 15, each arm 50 includes a first end connected to the hub 19 and/or other arms 50 and a second free end formed by the outer portion of the loop 52. At least the portion of each arm 50 that is unconnected to the other arms 50 of the unitary arm structure is freely movable, i.e., it is movable independently from the other arms 50. Each arm 50 is formed by a loop 52 and may include a web 54 having at least one radial strut 56 and several cross struts 57. The free end of each arm 50 may include a hole containing a marker 58.

With regard to the shape of each arm 50, thermal processing is used to impart a parent shape, as is known in the art. A preferred parent shape is shown in FIG. 15. This curved shape (shown in side view) for the right atrial anchor 14 presents a concave shape to the right atrial wall. This parent shape helps insure that the entire right atrial anchor will be apposed to atrial tissue once implanted. This apposition serves to minimize the chance for excessive thrombus formation and subsequent embolism, and also facilitates rapid incorporation of the anchor by adjacent atrial tissue.

The arms 50 form a unitary arm structure that is centered about a hub 19. Hub 19 is tubular, and is preferably formed of a radiopaque material such as platinum alloy. The inner diameter of the hub 19 is slightly larger than the diameter of the tether 16, to allow for the right atrial anchor 14 to slide relative to the tether 16. The hub 19 is secured to the unitary arm structure that forms the right atrial anchor 14 by swaging. A shoulder at the distal end of hub 19 is inserted inside the right atrial anchor 14, and flared by swaging, thus interlocking the hub 19 to the unitary arm structure, as shown in FIG. 15. The hub 19 is preferably about 0.090 inch to about 0.110 inch in length, with an enlarged ring 19*a* at the proximal end. This ring 19*a* facilitates removal or repositioning of the right atrial anchor 14 by a snare, as will be described later.

As embodied herein and shown in FIGS. 12 and 15, the right atrial anchor 14 may include a covering 60. Covering 60 provides assurance of complete closure of the PFO track, and facilitates tissue ingrowth into the right atrial anchor 14. The covering 60 preferably includes two layers, 60*a*, 60*b*, one on each side of the unitary arm structure that forms right atrial anchor 14. Alternatively, covering 60 may be a single layer attached on one side of the unitary arm structure. Preferably, the covering 60 is formed of a knitted or woven fabric of polyester, but may be formed from any suitable polymeric material such as expanded polytetrafluoroethylene. The covering 60 is secured to the unitary arm structure by suitable means, such as ultrasonically securing the two layers of fabric 60*a*, 60*b*, at their peripheries, and/or at locations between the arms 50 or within the loops 52. The covering 60 may be generally circular, as shown in FIG. 12, or any other suitable shape. The ends of arms 50 may also include small loops to receive sutures, for example, for suturing to the covering 60 of the unitary arm structure.

Figure 16:
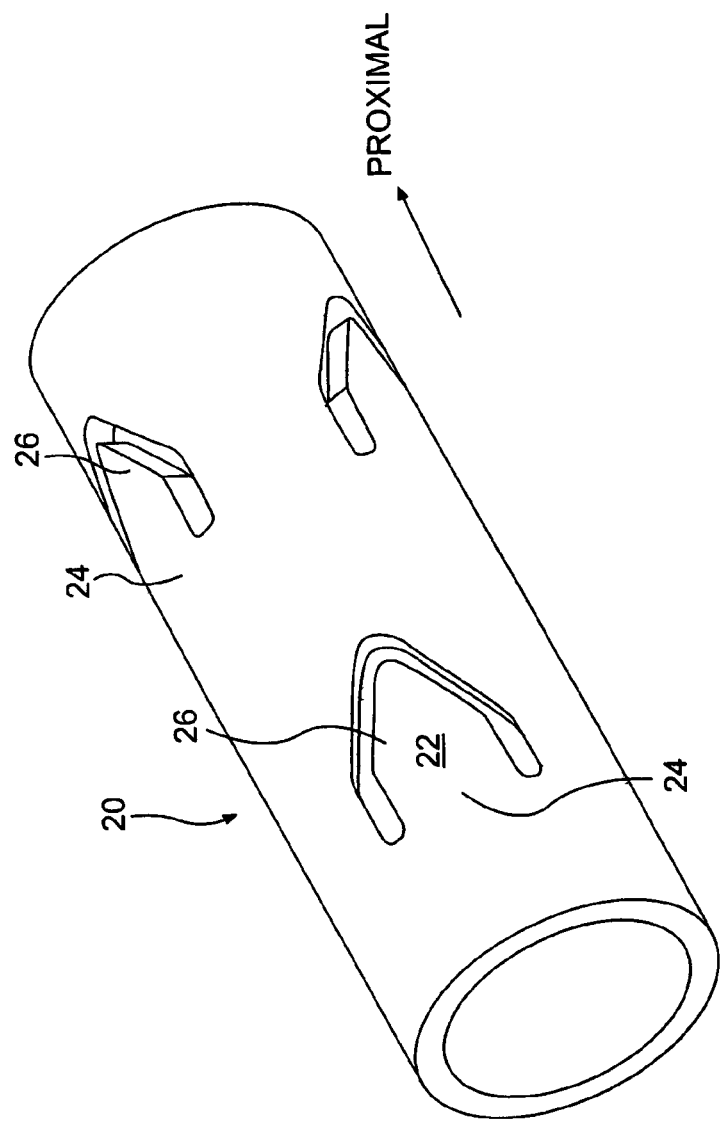
FIG. 16 is an isometric view of the lock used with the closure device in FIG. 14, according to an embodiment of the present invention.

Positioned proximally to right atrial anchor 14 on tether 16 is a lock 20. As embodied herein and shown in FIG. 16, the lock 20 is disposed about the tether 16. The lock 20 is tubular in shape and may be fabricated from a metallic material, such as a tube of nickel-titanium alloy. The inner diameter of the lock 20 is somewhat larger that the diameter of the tether 16, preferably about 0.010 inch to about 0.015 inch larger, and most preferably about 0.0125 inch larger. The lock 20 may have a wall thickness of between about 0.002 inch and about 0.005 inch, and most preferably about 0.003 inch. Lock 20 includes one or more tabs 22 formed in the tube. Preferably, lock 20 includes six tabs 22, three towards the distal end of the lock 20, and three towards the proximal end of the lock 20. The tabs towards the distal end are preferably circumferentially offset from the tabs towards the proximal end, better ensuring engagement of lock 20 with the tether 16. The tabs 22 may be formed by laser cutting. Each tab 22 includes a base 24, which connects to the main body of the lock 20, and a point 26, which serves to mechanically engage the tether 16. The tabs 22 are thermally shape set (as is known in the art) to have a parent shape with the tabs 22 deflected inward, such that the points 26 are forced to engage the tether 16. The points 26 engage the tether 16, by extending into the tether 16, when the lock 20 is moved relative to the tether 16 in one direction only. This allows the lock 20 to be advanced distally along the tether 16, while preventing proximal movement of the lock 20 along tether 16.

Figure 19:
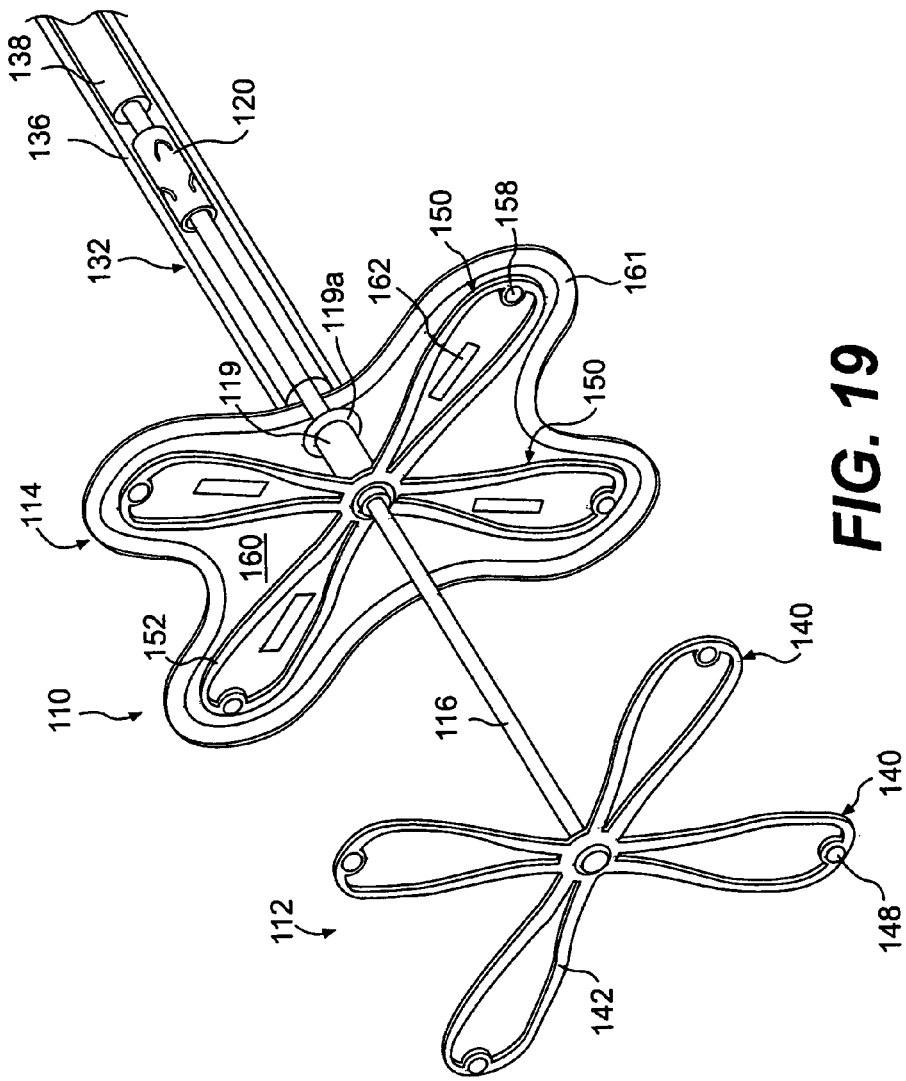
FIG. 19 is an isometric view of another embodiment of a closure device, according to the present invention.

FIG. 19 shows an alternative embodiment of a closure device 110. In at least some respects, the closure device 110 is similar to device 10 described with respect to FIGS. 12 and 15. Similar elements will be labeled with similar reference numerals in the Figure, and the differences between the embodiments will be explained. As embodied herein and shown in FIG. 19, the arms of closure device 110 may not include a web structure. Closure device 110 includes a left atrial anchor 112, a right atrial anchor 114, and a tether 116. Each anchor 112, 114, includes arms 140, 150, respectively. As shown in FIG. 19, each arm 140, 150, may be formed by a loop 142, 152, as previously described with respect to device 10. Arms 140, 150 may also include markers 148, 158, respectively, as previously described.

Additionally, the cover 160 for the right atrial anchor 114, as shown in FIG. 19, may be lobular in shape, instead of circular. Cover 160 also preferably includes two layers to effectively sandwich the arms 150. The two layers are preferably secured together at their peripheries 161 as shown, as well as at discrete locations 162 within the loops 152. The layers 160a, 160b, are secured by suitable means, such as by ultrasonic welding. The cover 160 could also be incorporated in any of the other embodiments of closure devices described in this application.

Figure 20:
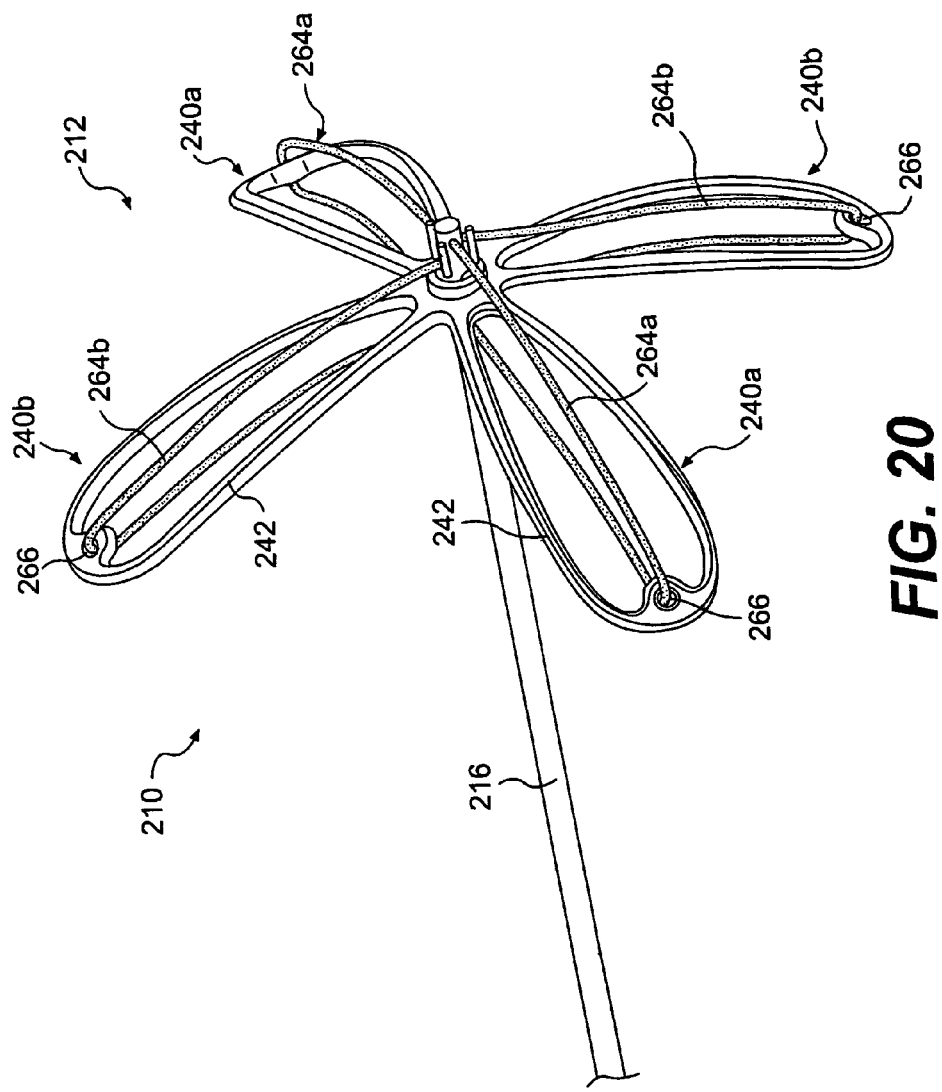
FIG. 20 is an isometric view of another alternative embodiment of a closure device, according to the present invention.
Figure 21:
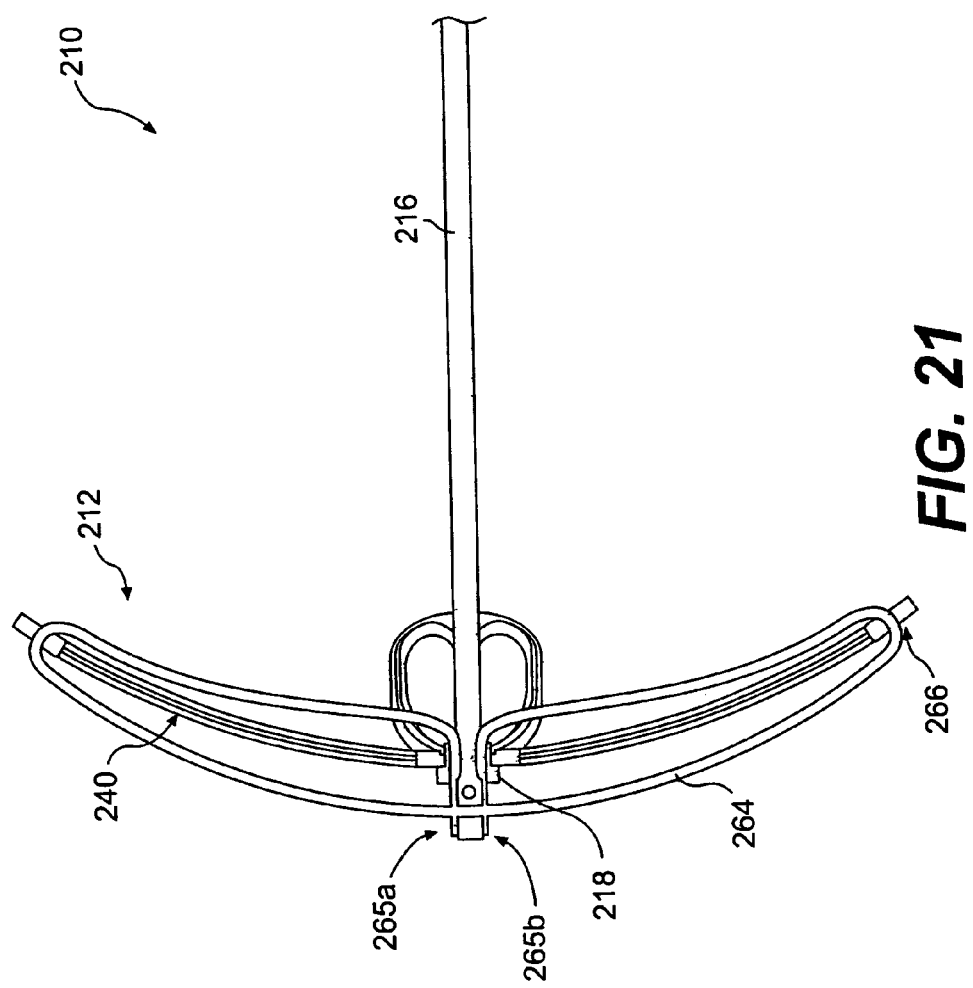
FIG. 21 is a side view of the closure device of FIG. 20.

FIGS. 20 and 21 show another alternative embodiment of a left atrial anchor 212 for a closure device 210. In at least some respects, left atrial anchor 212 is similar to left atrial anchor 112 described with respect to FIG. 19. Similar elements will be labeled with similar reference numerals in the Figures, and the differences between the embodiments will be explained. As embodied herein and shown in FIGS. 20 and 21, left atrial anchor 212 includes four arms 240. As previously discussed with respect to FIG. 19, arms 240 do not include a web structure, and are formed by loops 242. Each arm 240 may include a marker (not shown). Each left atrial arm 240 may further include a structure to prevent embolism of that arm 240, in the event of arm fracture. This structure performs a function similar to that the web 44, shown in FIG. 12, performs.

As shown in FIGS. 20 and 21, one or more safety lines 264 extend parallel to the arms 240 of the left atrial anchor 212. Two safety lines 264a, 264b are shown in FIG. 20. A first safety line 264a secures two arms 240a of the anchor 212, and a second safety line 264b secures the remaining arms 240b. Each safety line 264a, 264b is preferably formed of a flexible but strong polymeric material, such as a braided filament bundle of polyester or ultra-high molecular weight polyethylene. The safety lines 264 preferably pass through the ends of the arms 240 through holes 266. Although not shown, additional holes may be provided near the ends of the arms to contain markers, as described above. The preferred path for each safety line 264 is shown in FIG. 21. The two ends 265a, 265b of the safety line 264 lie next to the distal end of the tether 216. The safety line 264 extends through the hub 218, then along and parallel to two arms 240, through the holes 266, back along and parallel to the two arms 240, and then through the body of the tether 216 itself at a very distal end.

Alternatively, each arm 240 may include a separate safety line 264. For example, the end 265 of the line 264 could be adjacent the end of the tether 216 as described above, extend through the hub 218 and parallel to the arm 240 to the hole 266, and terminate in a knot or encapsulated fray at a hole (not shown) in the end of the tether 216, as previously described in connection with the distal end of the tether 216.

FIG. 13 shows the closure device 10 positioned relative to an embodiment of a delivery catheter 32. As embodied herein and shown in FIGS. 12, 13, 17, and 18, the delivery catheter 32 includes an outer tube 36 and an inner tube 38. The outer tube 36 may be formed from a polymer, preferably high density polyethylene. The distal portion 36b of the outer tube 36 preferably has an inner diameter of between about 0.040 inch and about 0.060 inch, and is most preferably about 0.048 inch, with a wall thickness of between about 0.005 and about 0.010 inch, and most preferably about 0.008 inch. As shown in FIG. 17, the distal portion 36b of the outer tube 36 may taper along its length to the most distal end. Alternatively, the distal portion 36b of the outer tube may have a constant inner and outer diameter. The proximal portion of the outer tube 36 preferably has an inner diameter of between about 0.050 inch and about 0.070 inch, and is most preferably about 0.060 inch, with a wall thickness of between about 0.005 inch and about 0.010 inch, and most preferably about 0.007 inch. The dimensions of the outer tube 36 are such that it can engage and abut with the hub 19 of the right atrial anchor 14 during the delivery of the device 10. The proximal end of the outer tube 36 includes a rigid sleeve 36a, formed of a hypotube which surrounds the polymeric tube. The rigid sleeve 36a serves to prevent kinking of the outer tube 36 during the delivery of the device. The length of the proximal rigid sleeve 36a is preferably between about 10 cm and about 20 cm, and is most preferably about 14 cm. The length of the outer tube 36, including the rigid sleeve 36a, is preferably between about 100 cm and about 130 cm, and is most preferably about 115 cm.

The inner tube 38 of delivery catheter 32 may be formed from a suitable polymer, such as PEBAX 6333™, and have a preferred inner diameter of between about 0.020 inch and about 0.040 inch, most preferably about 0.030 inch, with a wall thickness of between about 0.003 inch and about 0.010 inch, and most preferably about 0.006 inch. The preferred dimensions of the inner tube 38 are such that it can engage and advance the lock 20 along the tether 16. The distal end 38b of the inner tube 38 preferably has a uniform inner and outer diameter. The proximal end of the inner tube 38 also includes a rigid sleeve 38a, formed of a hypotube surrounding the polymeric tube. The length of the rigid sleeve 38a is preferably between about 15 cm and about 30 cm, and is most preferably about 23 cm. The length of the inner tube 38, including the rigid sleeve 38a, is preferably between about 90 cm and about 110 cm, and is most preferably about 100 cm.

In FIGS. 12 and 13, left atrial anchor 12 and right atrial anchor 14 are shown deployed from delivery catheter 32. As shown in FIG. 13, delivery catheter 32 may be used with a guide catheter 30. Although not shown, guide catheter 30 may have a pre-formed curve near its distal end. Guide catheter 30 can be any suitable, conventional guide catheter. A suitable, exemplary guide catheter is known as "Mullins" guide catheter, sold commercially by Cook. Connected to the proximal end of guide catheter 30 is a hemostasis valve 31.

Prior to deployment of closure device 10, guide catheter 30 would be delivered by conventional techniques to the site of the PFO. Such conventional techniques may include the temporary use of a guide wire (not shown).

Figure 14:
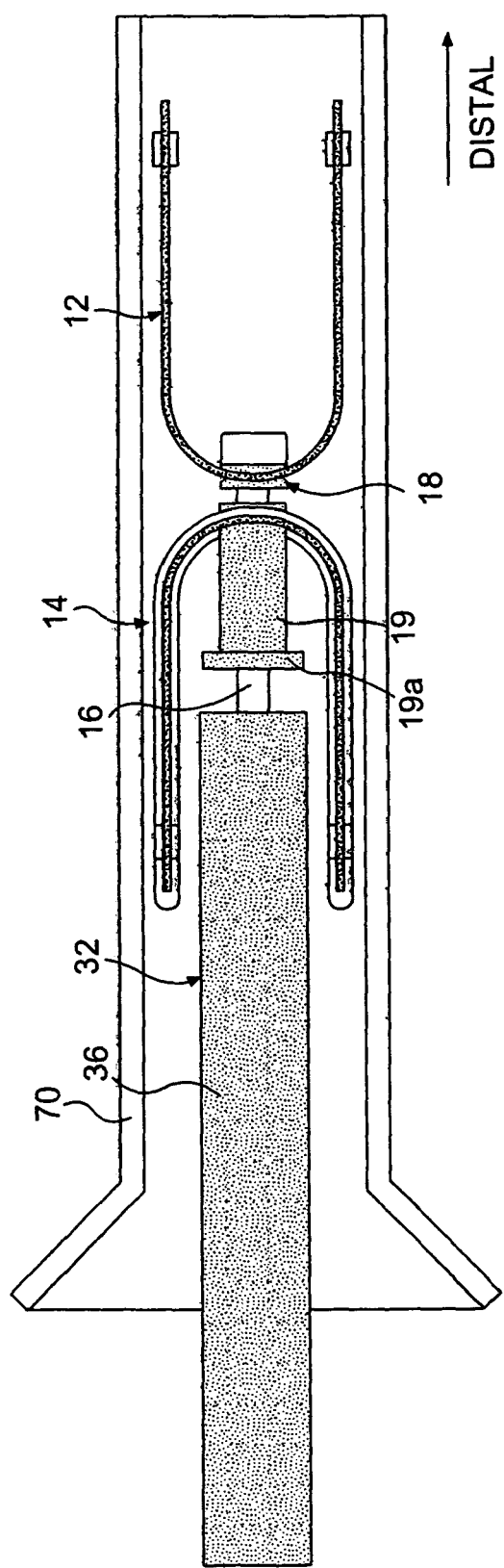
FIG. 14 is a cross sectional side view of a closure device and a delivery catheter positioned in a loading tube prior to introduction into a guide catheter, according to an embodiment of the present invention.

FIG. 14 illustrates the closure device 10 in a collapsed condition prior to delivery, within a loading tube 70. As shown in FIG. 14, loading tube 70 preferably has a flared proximal end to facilitate introduction of the device 10 and delivery catheter 32 into the loading tube 70. This is the state of the closure device 10 and delivery catheter 32 prior to introduction into the previously placed guide catheter 30. As shown in FIG. 14, the outer tube 36 of the delivery catheter 32 has a size that will abut the hub 19 of right atrial anchor 14 as tube 36 moves along tether 16. The right atrial anchor 14 also may move along tether 16 to abut the left atrial anchor 12. This abutment allows the left and right atrial anchors 12, 14 to move in response to movement of the delivery catheter 32 within the guide catheter 30. The condition in which the structures abut one another may be created and maintained by having the tether clip 34 positioned against the proximal end of the delivery catheter 32, after removing any initial slack in the tether 16. As shown in FIG. 14, the arms 40 of the left atrial anchor 12 are collapsed in the distal direction, while the arms 50 of the right atrial anchor 14 are collapsed in a proximal direction.

Figure 3:
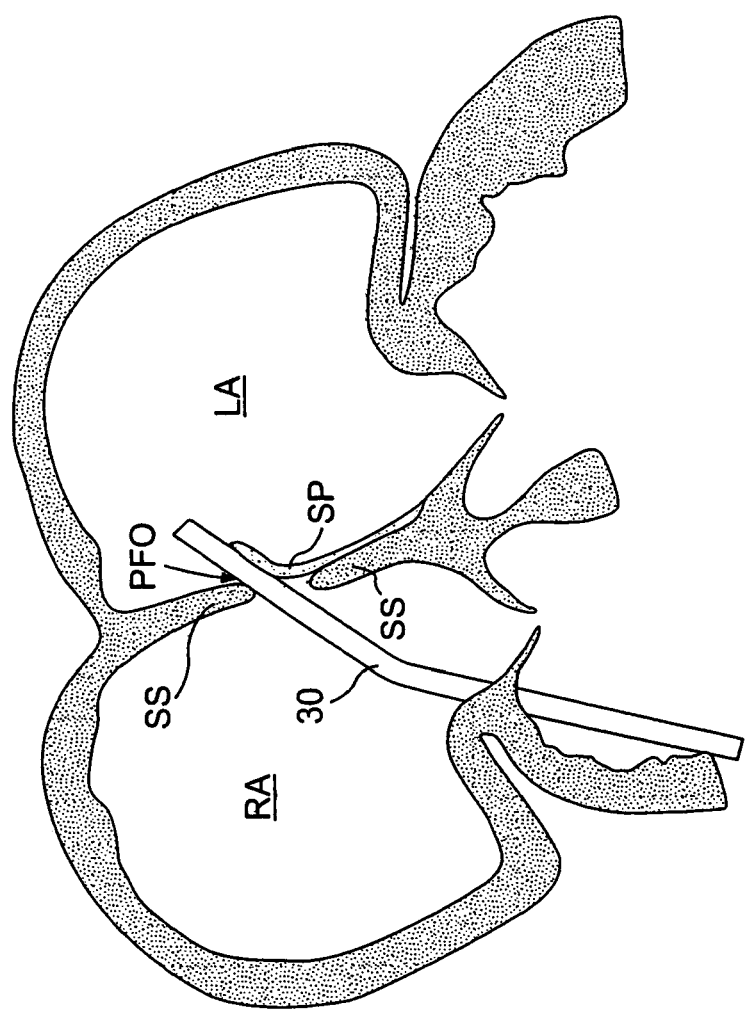
FIG. 3 is a guide catheter inserted through a PFO and into the left atrium, according to an embodiment of the present invention.

FIGS. 3-11 show sequential steps for delivery of closure device 10, according to one aspect of the invention. At the level of the longitudinal section shown in FIG. 3, the inferior vena cava (IVC) is not shown. In an embodiment, a delivery system is passed through the IVC to gain access to the RA and PFO. Other methods of percutaneously, minimally invasively, or more directly obtaining access to the RA and PFO are within the scope of the invention. As embodied herein and shown in FIG. 3, a guide catheter 30 is advanced to and through the PFO track and into the LA. The guide catheter 30 extends across the PFO track, as shown in FIG. 3. The proximal end of the guide catheter 30 includes a hemostasis valve 31. The loading tube 70, the collapsed closure device 10, and delivery catheter 32 are introduced into the guide catheter 30 through the hemostasis valve 31. When fully inserted into the hemostasis valve 31, the distal end of the loading tube 70 abuts the hub (not shown) of the guide catheter 30, preventing the loading tube 70 from continuing to advance down the lumen of the guide catheter 30. The collapsed closure device 10 is then advanced out the loading tube 70 by advancement of the delivery catheter 32 into the lumen of the guide catheter 30. Advancement of the delivery catheter 32 and collapsed closure device 10 continues until the closure device 10 is near the distal end of the guide catheter 30. The loading tube 70 is then withdrawn out of the hemostasis valve 31 and positioned on the delivery catheter 32 towards the proximal end. The hemostasis valve 31 is then closed to stop back bleeding.

Figure 4:
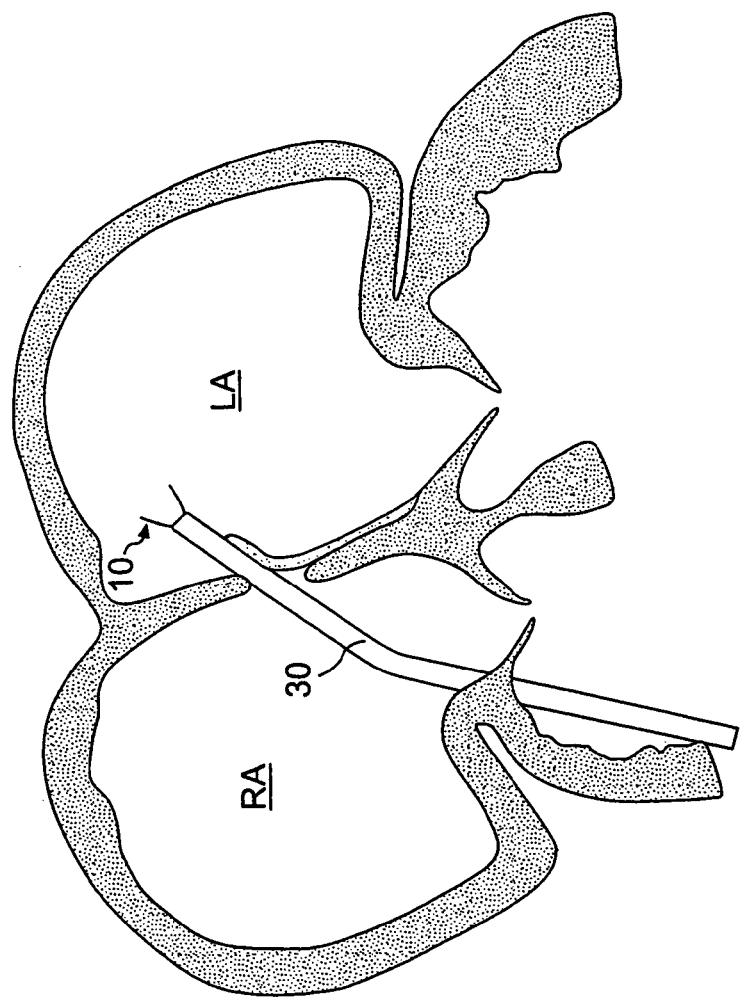
FIG. 4 is a left atrial anchor of the closure device of FIG. 2 being advanced out of the guide catheter, according to an embodiment of the present invention.
Figure 5:
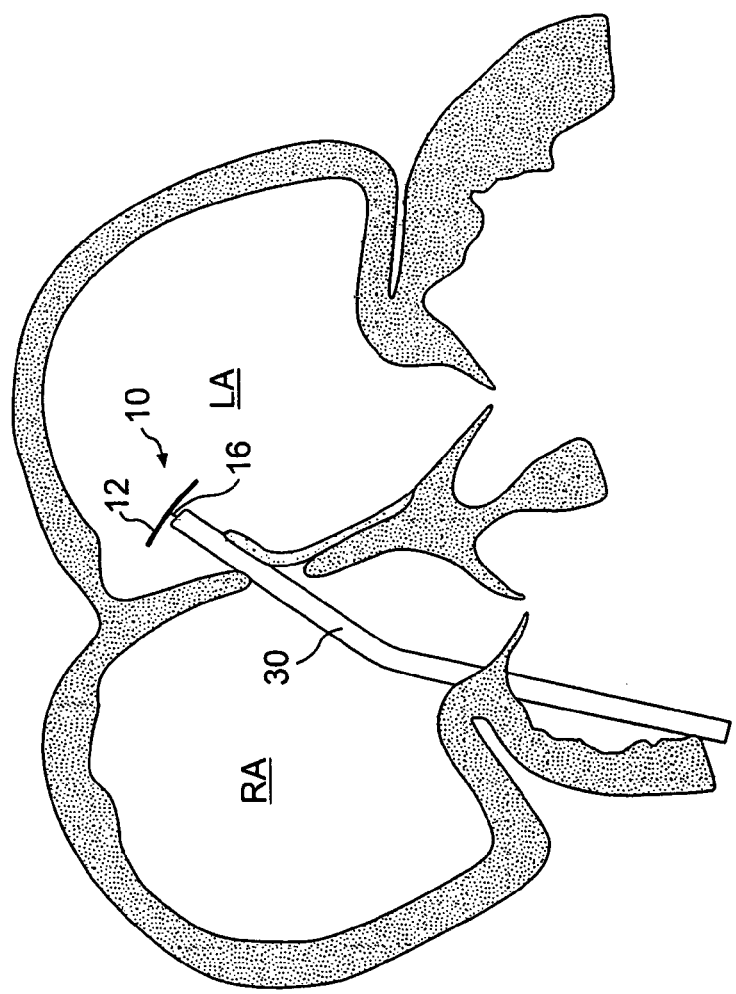
FIG. 5 is the left atrial anchor of the closure device of FIG. 4 advanced out of the guide catheter, according to an embodiment of the present invention.

The delivery catheter 32 is further advanced relative to the guide catheter 30, deploying only the left atrial anchor 12, as shown in FIGS. 4 and 5. FIG. 5 shows the left atrial anchor 12 fully deployed from the guide catheter 30 in the left atrium. Tether 16 extends from anchor 12 into guide catheter 30 and through delivery catheter 32. As discussed above, left atrial anchor 12 and right atrial anchor 14 are preferably self-expanding structures, expanding through a mechanical or thermal shape change, for example. Also at this point, right atrial anchor 14 remains within the delivery assembly in a collapsed state.

Figure 6:
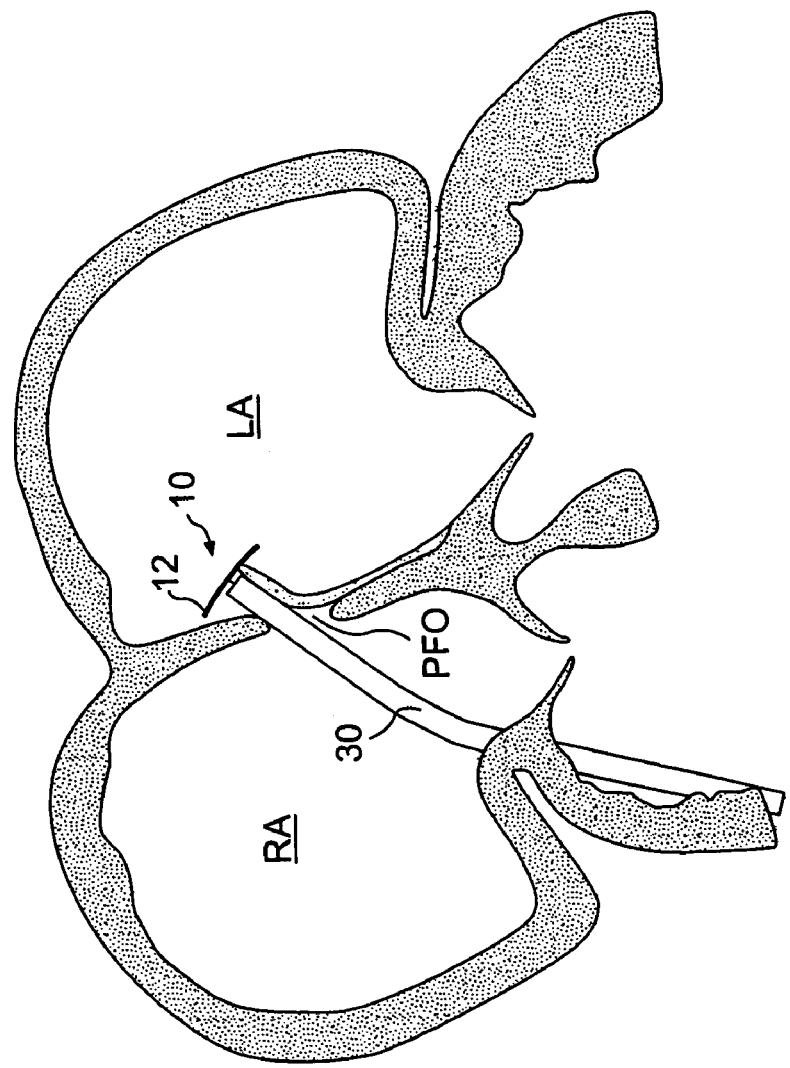
FIG. 6 is the left atrial anchor of FIG. 5 being pulled towards the PFO, according to an embodiment of the present invention.

The delivery catheter 32 and guide catheter 30 are withdrawn, pulling the left atrial anchor 12 against the opening of the PFO track, as shown in FIG. 6. As the tether clip 34 remains in the initial position abutting the proximal end of the delivery catheter 32, the left atrial anchor 12 is pulled against the opening of the PFO track. Next, the tether clip 34 is re-positioned several centimeters proximally on the tether 16.

Figure 7:
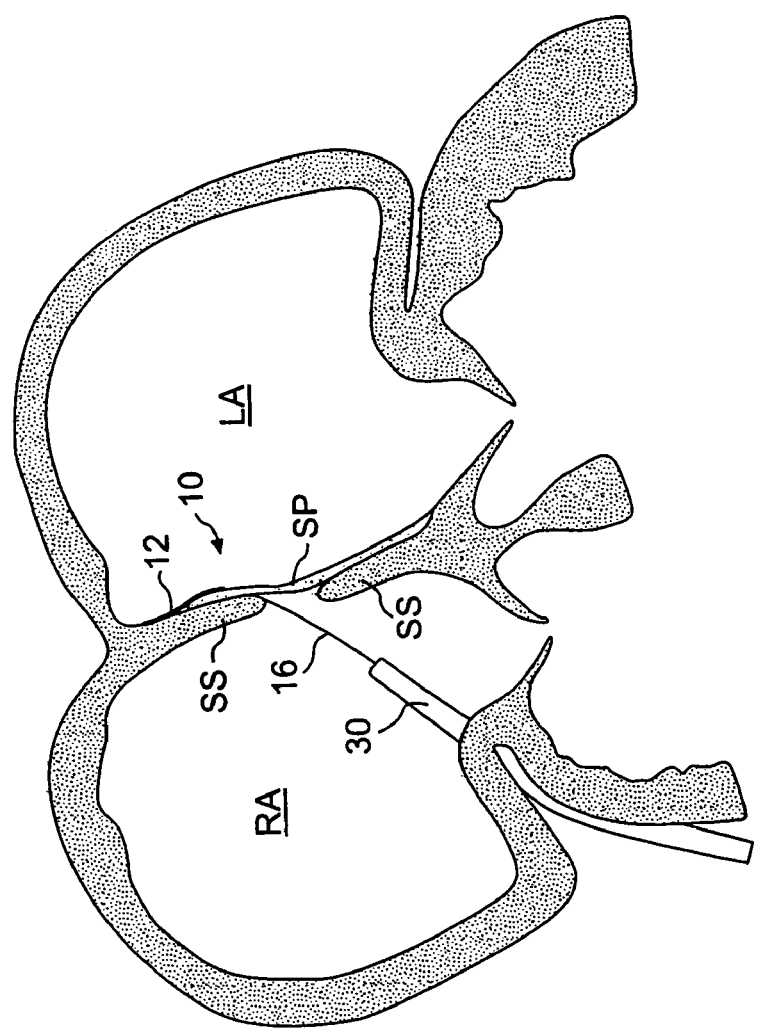
FIG. 7 is the guide catheter pulled proximally into the right atrium and the left atrial anchor seated against a septal wall, according to an embodiment of the present invention.

As shown in FIG. 7, a significant portion of the PFO track (specifically the portion of the track between the superior portion of the septum primum and septum secundum) runs along and roughly parallel with the septal wall. A feature of closure device 10 according to this embodiment is that left atrial anchor 12 and tether 16 are flexibly connected, and tether 16 is itself preferably flexible, to allow tether 16 to extend through the PFO track, while left atrial anchor 12 remains significantly apposed to the left atrial surface. Tether 16 is able to extend from left atrial anchor 12 at an obtuse angle. In many instances, left atrial anchor 12, with tension applied from tether 16, may mechanically close and thereby seal the PFO by bringing the septum primum (SP) into sealing contact with the septum secundum (SS). The effectiveness of this seal can be tested at this time by conventional techniques, such as contrast visualization, or a Valsalva maneuver combined with injection of bubbles, visualized with transesophageal ultrasound or intracardiac ultrasound. If the seal is ineffective, closure device 10 can be removed as described later, and exchanged for a different device. Alternatively, the device 10 can be repositioned as will be described below.

The guide catheter 30 and delivery catheter 32 are further withdrawn relative to the PFO track, until the distal end of the guide catheter 30 is well within the right atrium, as shown in FIG. 7. The right atrial anchor 14, still collapsed within the lumen of the guide catheter 30, moves together with the guide catheter 30 and delivery catheter 32. With the tether clip 34 previously positioned proximally, the catheters 30, 32 and the collapsed right atrial anchor 14 can freely slide proximally relative to the tether 16 and the left atrial anchor 12.

Once left atrial anchor 12 is positioned, right atrial anchor 14 may be deployed. As shown in FIG. 7, initial deployment of right atrial anchor 14 is preferably performed with the delivery catheter and the collapsed right atrial anchor 14 withdrawn sufficiently away from left atrial anchor 12 and the right atrial septal wall, so that right atrial anchor 14 does not impinge on the wall when it initially expands. This also assures that right atrial anchor 14 will not inadvertently deploy in the PFO track or the left atrium. Because right atrial anchor 14 is not permanently attached to tether 16, anchor 14 is free to be positioned in such a location away from the right atrial septal wall.

Figure 8:
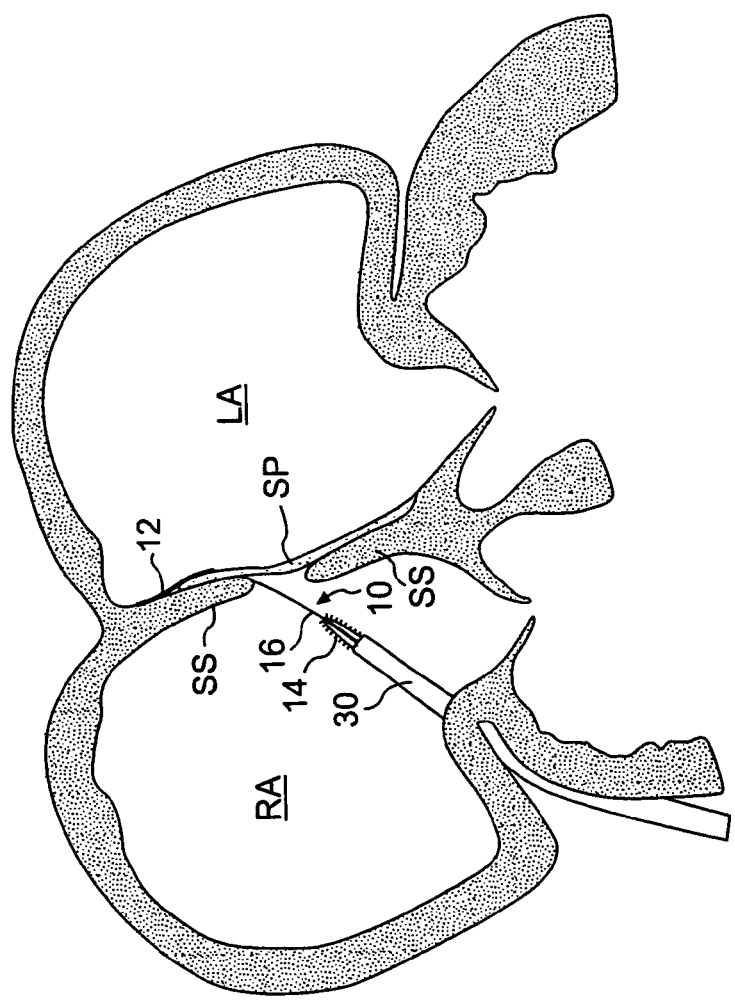
FIG. 8 is a right atrial anchor of the closure device of FIG. 2 being extended from the guide catheter, according to an embodiment of the present invention.
Figure 9:
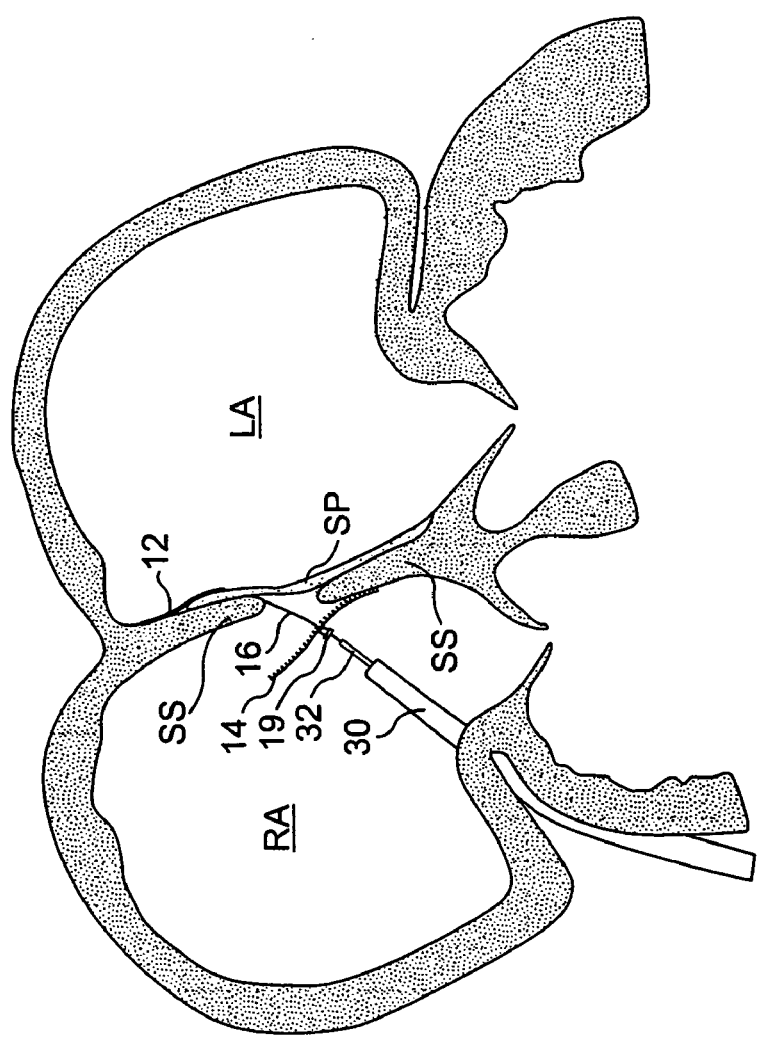
FIG. 9 is the right atrial anchor deployed from the guide catheter, according to an embodiment of the present invention.
Figure 10:
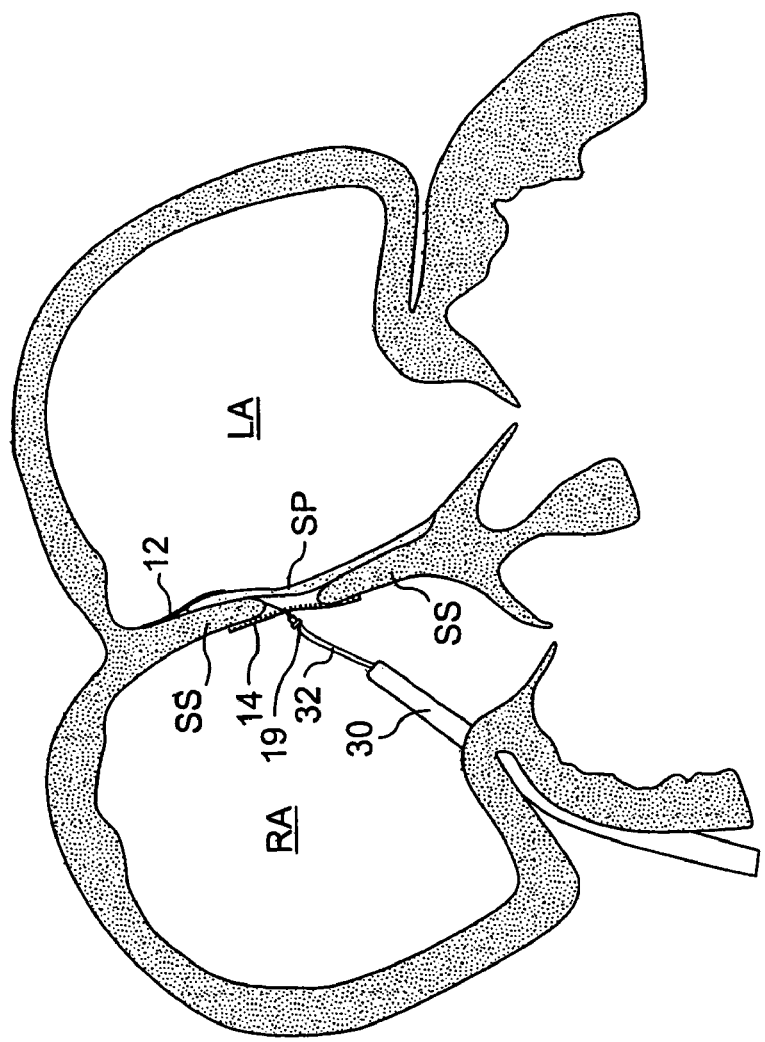
FIG. 10 is the right atrial anchor advanced to contact the septal wall, according to an embodiment of the present invention
Figure 11:
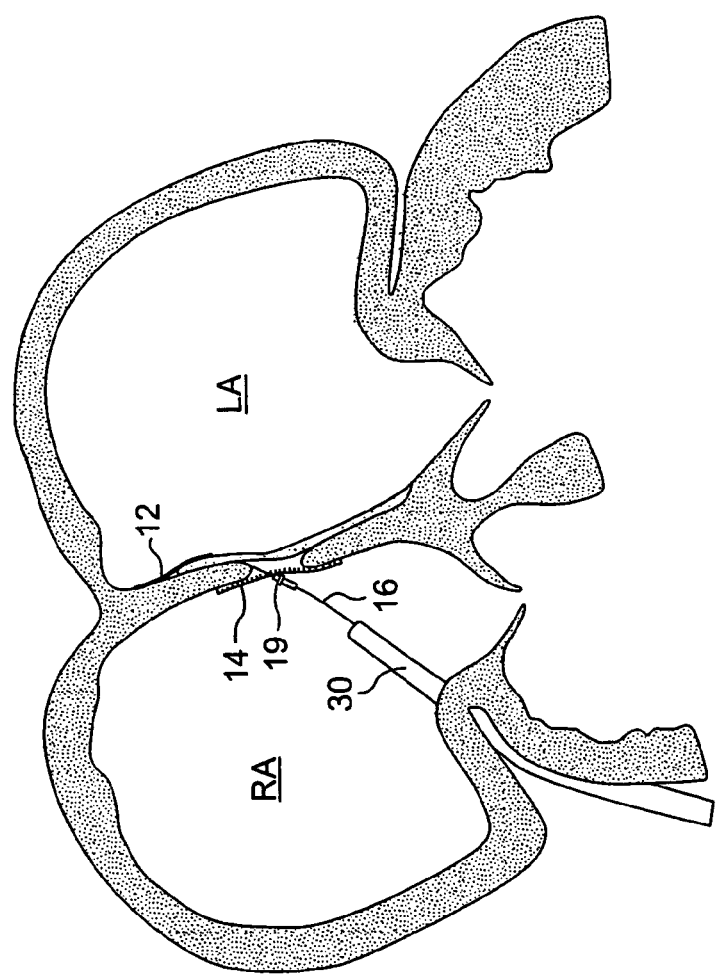
FIG. 11 is the right atrial anchor fixed to a tether of the closure device of FIG. 2, according to an embodiment of the present invention.

With the guide catheter 30 positioned in the right atrium, the right atrial anchor 14 is deployed by advancing the delivery catheter 32 relative to the guide catheter 30, as shown in FIGS. 8-10. This relative movement results in full deployment of right atrial anchor 14 within the right atrium RA, as shown in FIG. 9 At this stage of the delivery method, tether 16 passes through right atrial anchor 14 and preferably extends continuously through delivery catheter 32 and guide catheter 30 to the proximal end of the delivery catheter 32. Light tension is maintained on the tether 16 from the proximal end to prevent slack on the portion of the tether 16 between the left and right atrial anchors 12, 14.

In the next step of this embodiment of a closure device delivery method, right atrial anchor 14 is advanced into contact with the right atrial septal wall, as shown in FIG. 10. This is accomplished by advancing right atrial anchor 14 and delivery catheter 32 along tether 16 until right atrial anchor 14 is in a desired position relative to left atrial anchor 12, the septal wall, and the PFO, and has a desired amount of tension on left atrial anchor 12. It is preferred that left atrial anchor 12 have sufficient tension applied that the septum primum (SP) is brought into sealing apposition with the septum secundum (SS). This apposition, in many cases, may be enough to effectively close and seal the PFO. If desired, at this point in the delivery method, the effectiveness of the closure and seal can again be tested by conventional techniques, such as those described above. If the seal is ineffective, closure device 10 can be removed as described later, and exchanged for a different device (e.g., one of a different size). Alternatively, the device 10 can be repositioned as described later.

The right atrial anchor 14 is advanced until it makes contact with the right atrial end of the PFO track, thus closing it off. The tether clip 34 is then repositioned back to abut the proximal end of the delivery catheter 32 to temporarily maintain the relative positions of the left and right atrial anchors 12, 14. A test of the effectiveness of the closure of the PFO track can then be performed, as described earlier. Note that the distal end of the delivery catheter 32 is not fully connected to the right atrial anchor 14, but is merely abutting it. This arrangement allows for the delivery catheter 32 to pivot relative to the right atrial anchor 14 when abutting the right atrial anchor 14, as shown in FIG. 10. Therefore, the natural orientation that the right atrial anchor 14 takes as it conforms to the wall of the right atrium is not impacted by the orientation of the delivery catheter 32 (or guide catheter 30), enabling the position of the PFO closure device 10 to accurately represent the final state of closure, once the tether is cut and all catheters removed.

Up to this point, the two primary components of the delivery catheter 32, the inner tube 38 and the outer tube 36, have been secured together by way of a touhy-borst fitting 33 in a y-adaptor 35 at the proximal end of the outer tube 36, as shown in FIG. 13. The touhy-borst fitting 33 is initially tightened to prevent relative movement between the inner tube 38 and the outer tube 36. The inner tube 38 initially extends several cm proximally of the touhy-borst fitting 33.

The lock 20, which is initially positioned on the tether 16, several cm proximal of the distal end of the tether 16, is now advanced distally to permanently secure the position of the right atrial anchor 14 relative to the tether 16. To advance the lock 20, the touhy-borst fitting 33 securing the inner tube 38 and the outer tube 36 is loosened. Then, the inner tube 38 is advanced while maintaining the position of the outer tube 36 against the right atrial anchor 14. To prevent creating slack on the tether 16, light tension is applied at its proximal end.

The lock 20 is advanced along the tether 16 under fluoroscopic visualization until it abuts the hub 19 of the right atrial anchor 14. At this point, the delivery catheter 32 is withdrawn several cm, and the PFO closure is re-assessed as discussed previously. In some instances, the right and left atrial anchors 12, 14 may need to be further tightened relative to each other. This can be done by re-advancing the inner tube 38 to the lock 20. The lock 20 is then incrementally advanced along the tether 16, shortening the length of the tether 16 between the left and right atrial anchors 12, 14.

At this point, the effectiveness of the closure and sealing of the PFO can be tested by conventional techniques, such as contrast visualization, or a Valsalva maneuver combined with injection of bubbles, visualized with (TEE) or intracardiac ultrasound.

Figure 22:
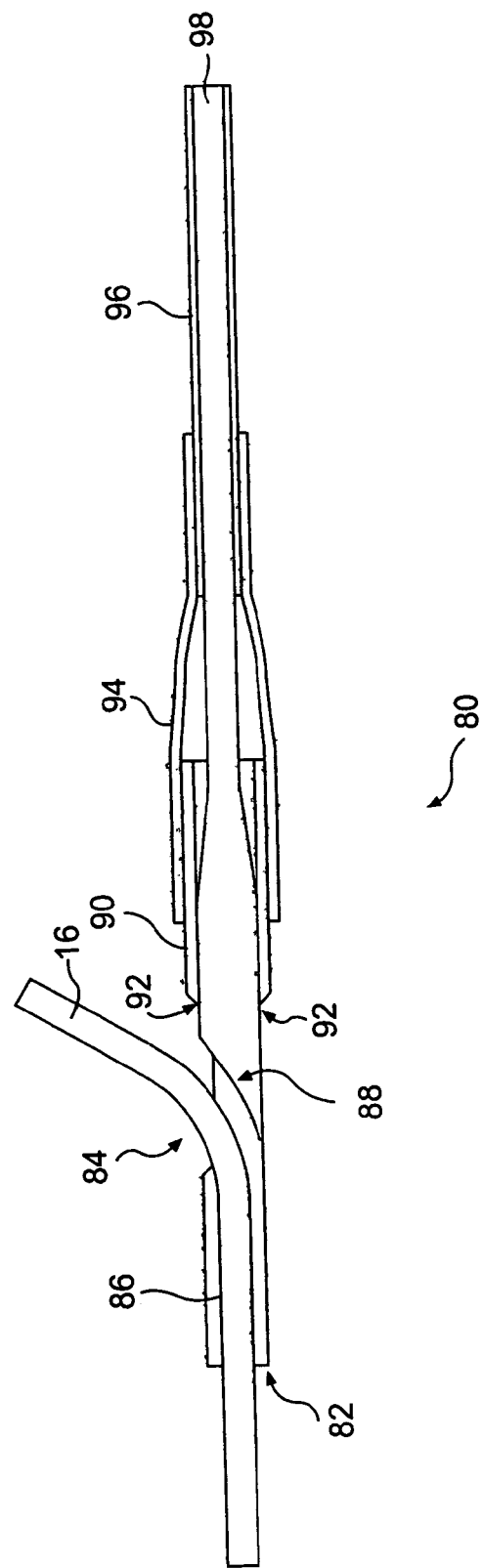
FIG. 22 is a cross-sectional side view of a portion of a cutting tool, according to one aspect of the present invention.

Once a satisfactory closure of the PFO track is confirmed, the tether 16 may be cut at a position near the right atrial anchor 14. A cutting tool 80 is used to perform this step. An embodiment of a cutting tool 80 is illustrated in FIG. 22. The cutting tool 80 includes a tubular cutting element 90, preferably formed of stainless steel, with a sharpened distal edge 92. The cutting element 90 is connected to an outer tube 96 via a linking portion 94. Outer tube 96 extends to the proximal end of the cutting tool 80. The outer tube 96 is preferably incorporates a wire braid (not shown) to impart a relatively high torsional stiffness.

The cutting element 90 surrounds a tether guide 86, preferably formed from metallic hypotubing, with an outer diameter close to the inner diameter of the cutting element 90. The tether guide 86 incorporates a distal opening 82. A lateral opening 84 is a short distance, preferably about 1 mm to about 5 mm proximal of the distal opening 82. The tether guide 86 is secured about the distal end of a central wire 98. The central wire 98, preferably made of stainless steel, extends proximally through the outer tube 96 to the proximal end of the cutting tool 80. The distal portion of the central wire 98 is enlarged to fill the inside diameter of the tether guide 86. The distal end of the central wire 98 further incorporates a bevel 88. Central wire 98 moves axially and rotationally relative to outer tube 96. At the proximal end of the cutting tool (not shown) is a handle mechanism, which facilitates controlled relative rotation and longitudinal movement between the central wire 98 and the outer tube 96.

The initial position of the cutting element 90 is just proximal to the lateral opening 84 in the tether guide 86, as shown in FIG. 22. The handle mechanism when activated causes the outer tube 96 and cutting element 90 to rotate relative to the central wire 98 and the tether guide 86. A screw or other suitable mechanism in the handle mechanism further causes the outer tube 96 and cutting element 90 to advance distally along the tether guide 86, until the cutting element 90 is just distal of the lateral opening 84 thereby severing tether 16.

In use, the cutting tool 80 is loaded over the proximal end of the tether 16, as shown in FIG. 22, the tether 16 being inserted in the distal opening 82 of the tether guide 86. The bevel 88 causes the tether 16 to emerge out the lateral opening 84. The cutting tool 80 is advanced along the tether 16 until the distal end of the cutting tool 80 abuts the lock 20. At this point, the handle mechanism is activated, which causes the cutting element 90 to advance and slice the tether 16. The PFO closure device 10 is now fully implanted.

There are several points during the delivery of closure device 10 where device 10 can be completely removed from the patient. This may be necessary if, for example, device 10 is not creating a complete seal due to any of a number of causes, including, for example, the selected device being too small.

For example, after deployment of the left atrial arm 12, but before deployment of the right atrial arm 14 (the position shown in FIG. 7), the deployed left atrial arm 12 can be captured by advancement of the guide catheter 30 relative to the tether 16 and left atrial anchor 12, which are fixed relative to the PFO track. The guide catheter 30 is advanced through the PFO track until it meets the left atrial anchor 12. The guide catheter 30 continues to advance, causing the left atrial anchor 12 to essentially resume the position it was in prior to initial deployment. Light tension is applied to the tether 16 during the advancement.

Alternatively, the device 10 may be retrieved after deployment of the right atrial anchor 14, but before advancement of the lock 20 (the position shown in FIG. 10). The deployed right atrial anchor 14 can be captured by use of a snare catheter (not shown). A preferred snare catheter is commercially available by Microvena (ev3), and sold under the trade name Amplatz Gooseneck Snare. The outer tube 36 of delivery catheter 32 is left in place abutting the right atrial anchor 14. The tether clip 34, y-adaptor, and the inner tube 38 of delivery catheter 32 are all removed from the tether in a proximal direction, leaving the outer tube 36 of delivery catheter 32 in place. The snare is advanced over the proximal end of the outer tube 36 of delivery catheter 32 and along the annular space between the guide catheter 30 and the outer tube 36 of delivery catheter 32. The snare is activated to engage the enlarged ring 19a on the hub 19 of the right atrial anchor 14. Then the snare, together with the outer tube 36 of delivery catheter 32, is withdrawn relative to the guide catheter 30 and tether 16. Continued proximal movement of the snare causes the right atrial anchor 14 to collapse into the guide catheter 30. Once the collapsed right atrial anchor is near the hemostasis valve 31 of the guide catheter 30, the loading tube 70 is re-advanced through the hemostasis valve 31. The collapsed right atrial anchor 14 is drawn into the loading tube 70, allowing the right atrial anchor 14, outer tube 36 of delivery catheter 32, and snare to be removed from the guide catheter 30. The left atrial anchor 12 then may be removed by advancing the guide catheter 30 through the PFO track, while maintaining tension on the tether 16. Once the guide catheter 30 contacts the left atrial anchor 12, continued advancement of the guide catheter 30 relative to the left atrial anchor 12 will cause it to collapse into the guide catheter 30, allowing subsequent removal.

Figure 23:
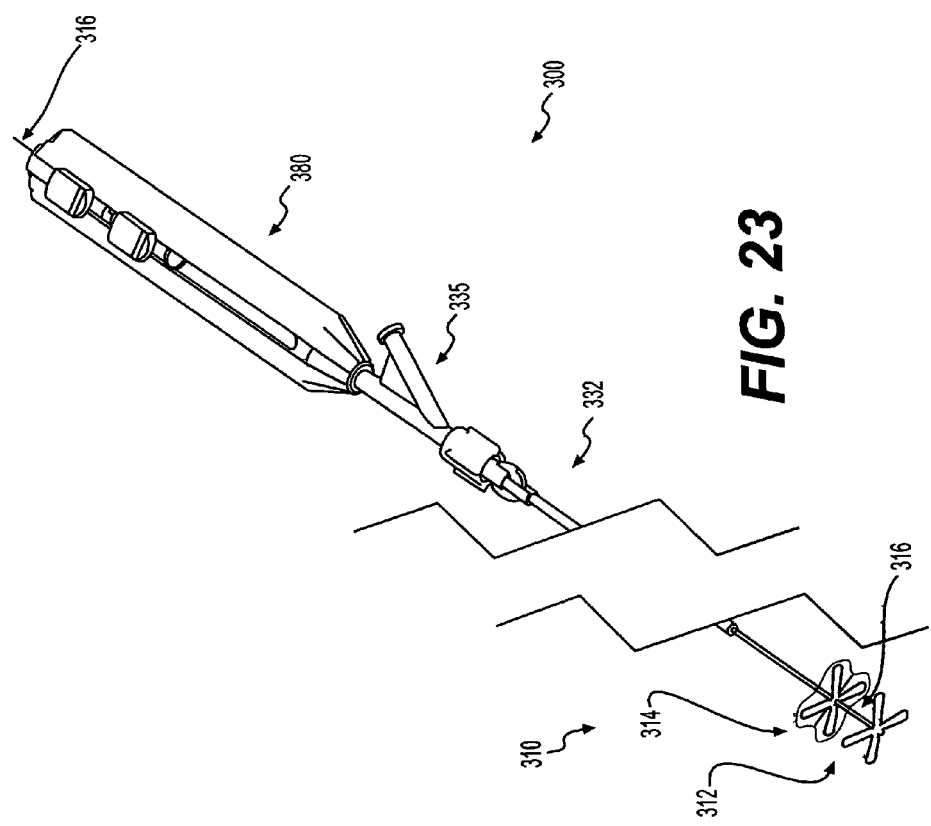
FIG. 23 is an isometric view of a closure device with a delivery system, according to an embodiment of the present invention.
Figure 24:
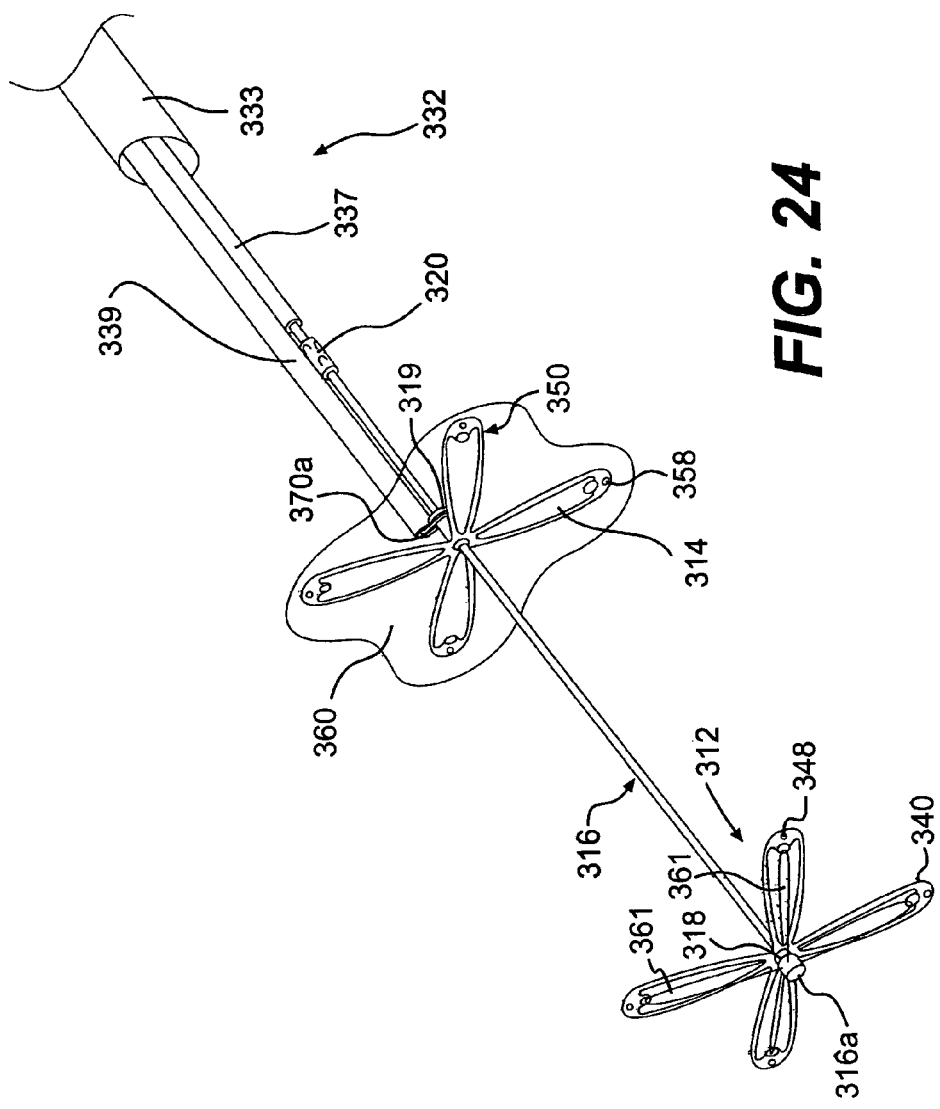
FIG. 24 is an isometric view of a closure device being delivered by the delivery system of FIG. 23.
Figure 29:
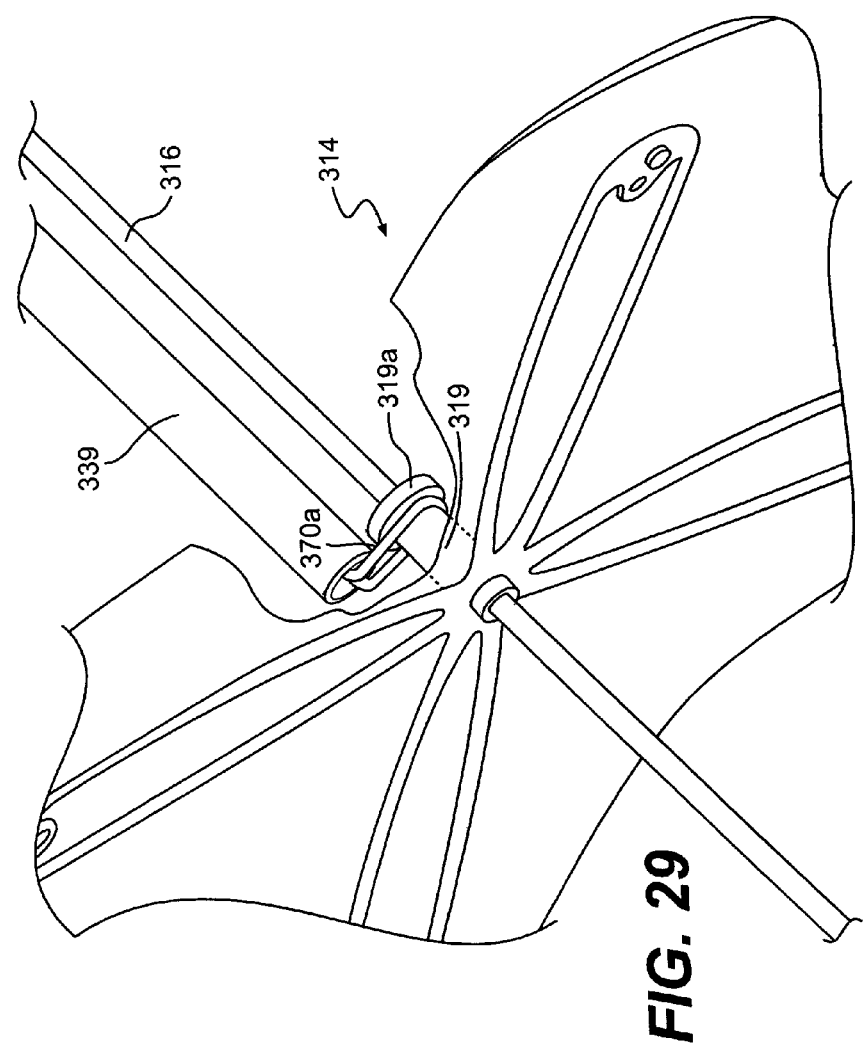
FIG. 29 is an enlarged partial view of a portion of a closure device that has been advanced out of a delivery catheter, according to one aspect of the present invention.

According to another aspect of the invention, a system 300 includes a closure device 310 and a delivery system for delivering the closure device 310. The delivery system may include side-by-side delivery tubes rather than coaxial delivery tubes. FIG. 23 shows a closure device 310 positioned relative to an embodiment of a delivery system 332. In at least some respects, the closure device 310 is similar to devices 10 and 110 described with respect to FIGS. 12, 15, and 19. Similar elements will be labeled with similar reference numerals in the Figures, and the differences between the embodiments will be explained. As embodied herein and shown in FIGS. 23 and 24, closure device 310 includes a left atrial anchor 312, a right atrial anchor 314, a tether 316, and a lock 320. Each anchor 312, 314, includes arms 340, 350, respectively, which extend radially outward from hubs 318 and 319, respectively. The hub 318 serves to engage the distal bulb 316a of the tether 316, as previously described and as shown in FIGS. 15 and 24. As shown in FIG. 29, the hub 319 includes an enlarged ring 319a at the proximal end. Ring 319a facilitates positioning and repositioning of the right atrial anchor 314 by a release wire of a release wire tube of a delivery system, as will be described later.

As shown in FIG. 24, each arm 340, 350, may be formed by a loop, as previously described with respect to device 10. Arms 340, 350 may also include markers 348, 358, respectively, such as rivets formed from a radiopaque material to assist in visualization of the device 10 during delivery. The cover 360 for the right atrial anchor 314, as shown in FIG. 24, may be lobular in shape, or may have any other suitable shape, such as circular. Cover 360 also preferably includes two layers to effectively sandwich the arms 350. The two layers are preferably secured together at their peripheries, as well as at discrete locations within the loops forming the arms. The layers are secured by suitable means, such as by ultrasonic welding.

In at least some aspects, left atrial anchor 312 is similar to left atrial anchor 212 described with respect to FIGS. 20 and 21. Similar elements will be labeled with similar reference numerals in the Figures. As embodied herein and shown in FIG. 24, left atrial anchor 312 includes four arms 340. Each left atrial arm 340 may include a structure to prevent embolism of that arm 340, in the event of arm fracture. This structure performs a function similar to that of safety line 261, as shown in and described with respect to FIGS. 20 and 21. As shown in FIG. 24, one or more safety lines 361 extend parallel to the arms 340 of the left atrial anchor 312, similar to the safety lines previously described with respect to FIGS. 20 and 21. Each safety line 361 is preferably formed of a flexible but strong polymeric material, such as a braided filament bundle of polyester or ultra-high molecular weight polyethylene. The safety lines 361 preferably pass through holes in the ends of the arms 340. As shown, additional holes may be provided near the ends of the arms to contain the radiopaque markers 348, as described above.

FIGS. 23 and 24 show the closure device 310 schematically in a deployed condition. As shown in FIGS. 23 and 24, left atrial anchor 312 is permanently secured to the distal end of the tether 316 via a hub 318 as described previously with respect to the embodiment shown in FIG. 21. Tether 316 extends through hub 318 to right atrial anchor 314. Right atrial anchor 314 is slidably disposed about the tether 316 via a second tubular hub 319. Lock 320 is advanceable along the tether 316, in a distal direction only, to secure the right atrial anchor 314 in position against the atrial tissue defining the PFO track. Tether 316 will be severed adjacent to lock 320; and left atrial anchor 312, right atrial anchor 314 connected to left atrial anchor 312 via tether 316, and lock 320 will remain in the heart to seal the PFO.

As shown in FIG. 23, the tether 316 extends through the right atrial anchor 314, through a delivery system 332 that passes through a lumen of a guide catheter (not shown), and emerges from the proximal end of the delivery system 332 and through a handle 380. As embodied herein and shown in FIG. 24, the delivery system 332 may include an outer delivery tube or catheter 333, a first inner tube or lock push tube 337, and a second inner tube or release wire tube 339. As embodied herein and shown in FIGS. 23 and 24, delivery tube 333 may be an outer tube that contains and provides support to the lock push tube 337 and the release wire tube 339. In such an embodiment, the lock push tube 337 and the release wire tube 339 may be inner catheters that are provided in and supported by outer delivery tube 333. Y-adaptor 335 allows fluid communication to the interior of outer tube 333 to facilitate priming/preparation of the system and delivery of fluids through the system. In an alternative embodiment, outer delivery tube 333 may not be provided, and lock push tube 337 and wire release tube 339 are provided in side-by-side relationship.

Figure 31A:
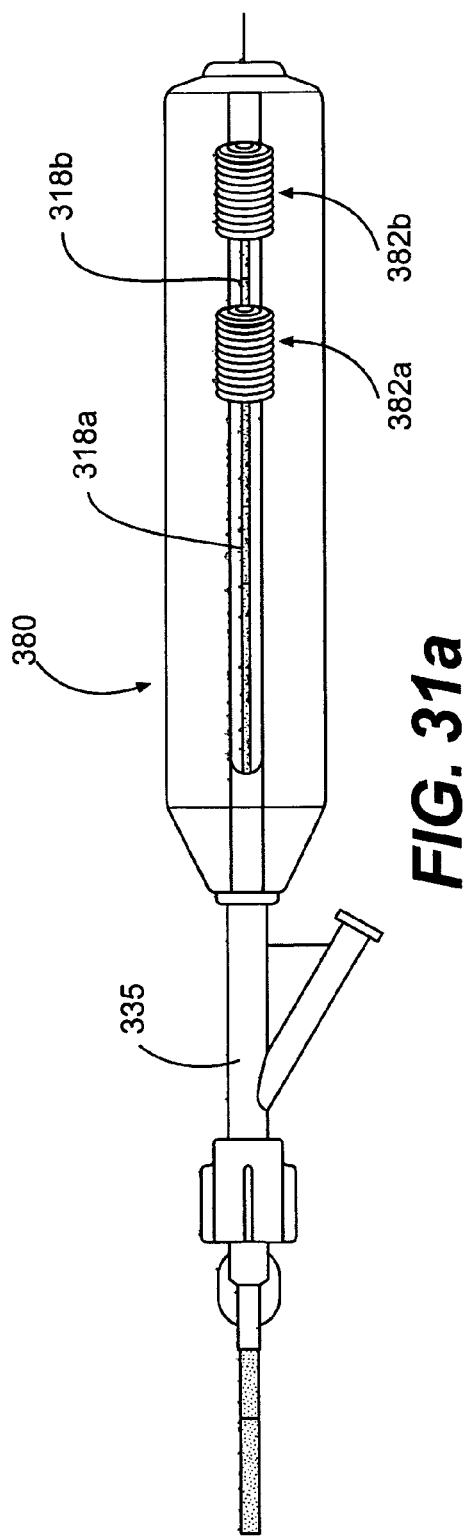
FIG. 31a is a top view of a handle of a delivery system prior to delivery of a closure device, according to one aspect of the present invention.
Figure 31B:
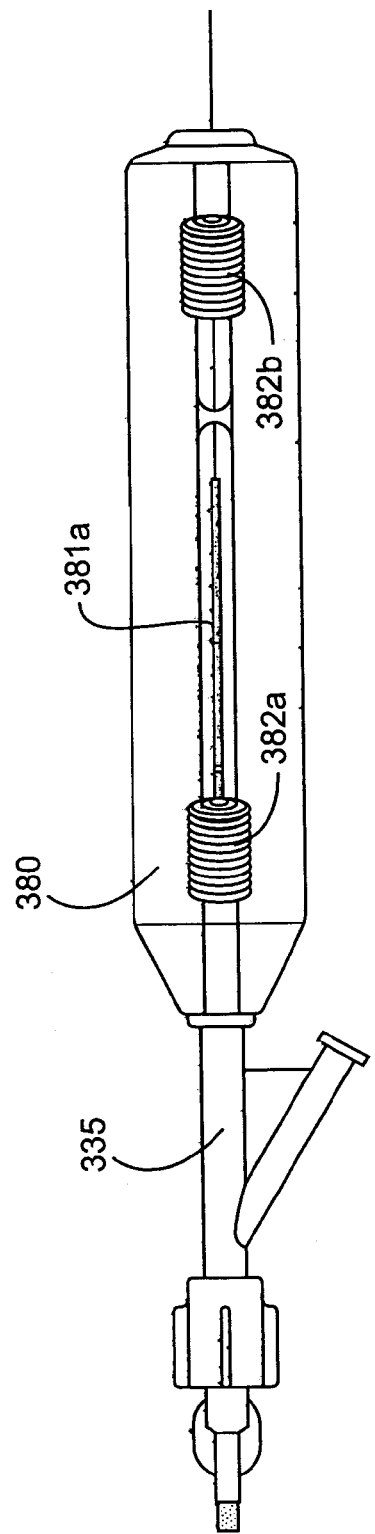
FIG. 31b is a top view of the handle of FIG. 31a after advancement of a lock of a closure device, according to one aspect of the present invention.
Figure 31D:
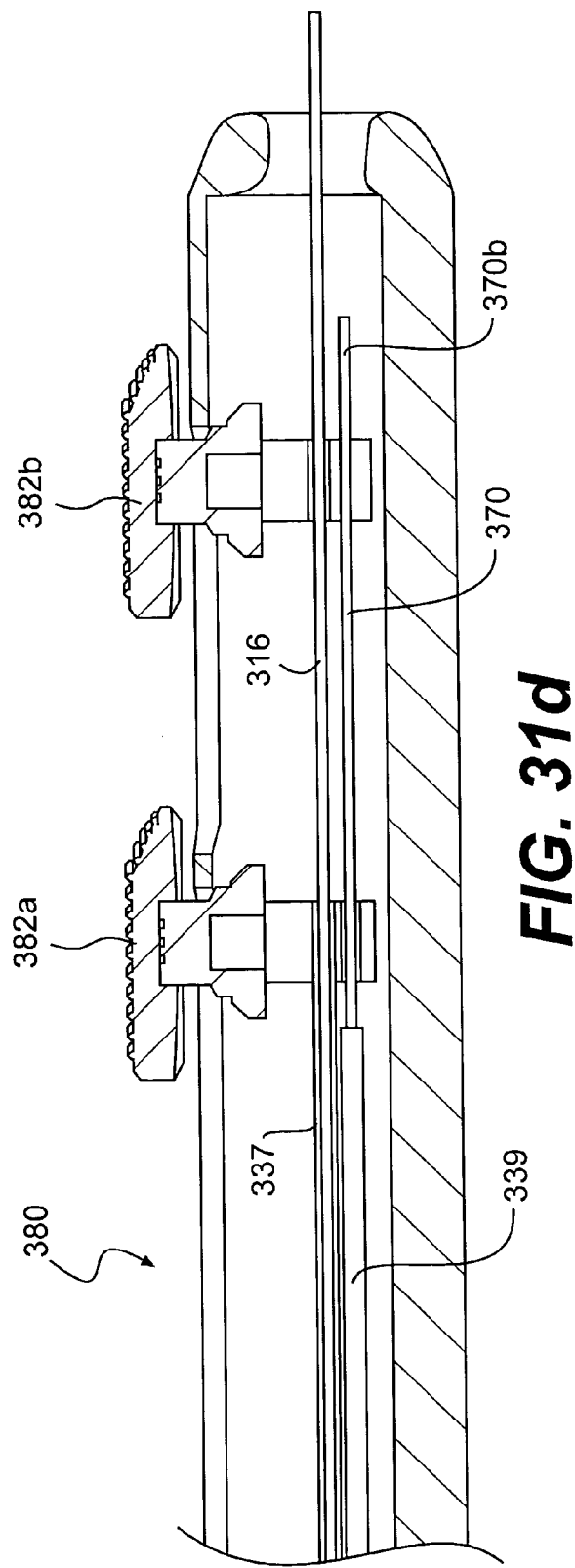
FIG. 31d is an enlarged cross-sectional portion of a rear portion of the handle of FIG. 31a, according to one aspect of the present invention.

A handle 380 may also be provided. As shown in FIG. 23, handle 380 is connected to y-adaptor 335, and y-adaptor 335 connects to outer delivery tube 333. As shown in FIGS. 24 and 31d, tether 316 extends through lock push tube 337, and emerges from the proximal end of the delivery system 332, through handle 380. As shown in FIG. 31a, handle 380 includes two actuatable elements, such as knobs 382a, 382b. Each actuatable element 382a, 382b, is configured to connect to and control movement of one of lock push tube 337 and a release wire 370, as will be described below. Lock push tube 337 and release wire tube 339 (containing release wire 370) extend in a side-by-side relationship into handle 380. Each of the first and second inner tubes 337, 339 is shown as having a round cross-sectional shape. However, each tube may have a different type of cross-sectional shape if desired.

The outer delivery tube 333 may be formed from a polymer, such as for example, PEBAX 7233™. The outer delivery tube 333 preferably has an inner diameter of between about 0.095 inch and about 0.115 inch, and is most preferably about 0.105 inches. The outer delivery tube 333 preferably has an outer diameter of between about 0.110 inch and about 0.130 inch, and is most preferably about 0.120 inches, with a wall thickness of between about 0.010 inch and about 0.020 inch, and most preferably about 0.015 inch. The dimensions of the outer delivery tube 333 are such that it can contain and support lock push tube 337 and wire release tube 339. The length of the outer delivery tube 333 is preferably between about 36.5 inch and about 42.5 inch, and is most preferably about 39.5 inches.

Lock push tube 337 may be formed from a suitable polymer, such as PEBAX 6333™, and may have a preferred inner diameter of between about 0.020 inch and about 0.040 inch, most preferably about 0.030 inch, with a wall thickness of between about 0.003 inch and about 0.010 inch, and most preferably about 0.006 inch. The preferred dimensions of the lock push tube 337 are such that it can engage and advance the lock 320 along the tether 316. The length of the lock push tube 337 is preferably between about 42.5 inch and about 48.5 inch, and is most preferably about 45.5 inches. Lock push tube 337 surrounds tether 316 and extends alongside release wire tube 339. As shown in FIG. 31d, the proximal end of lock push tube 337 may be connected to a portion of a first actuatable element such as first knob 382a of the handle 380. As shown in FIG. 31d, at least a portion of knob 382a sits outside handle 380 in a track 381a (see FIG. 31a) such that it is accessible by a system operator. First knob 382a is movable within the track 381a in the handle as shown in FIG. 31b. Moving knob 382a forward (distally) in its track moves lock push tube 337 and lock 320 in a distal direction along tether 316.

Wire release tube 339 may be formed from a suitable polymer, such as reinforced polyimide with a lubricious liner such as PTFE, and may have a preferred inner diameter of between about 0.023 inch and about 0.043 inch, most preferably about 0.033 inches. The wire release tube 339 may have a preferred outer diameter of between about 0.033 inch and 0.053 inch, most preferably about 0.043 inches, with a wall thickness of between about 0.005 inch and about 0.015 inch, and most preferably about 0.010 inches. The length of the wire release tube 339 is preferably between about 43.5 inch and about 49.5 inch, and is most preferably about 46.5 inches. Wire release tube 339 surrounds a release wire 370 and extends alongside lock push tube 337. The preferred dimensions of the wire release tube 339 are such that it permits release wire 370 to move through the tube. Preferably, the release wire 370 is folded in half such that its tail ends extend through a proximal end of the tube 339 while its folded end extends through a distal end of the tube to engage a portion of the right atrial anchor 314.

As discussed above, exemplary lengths have been provided for each of the outer delivery tube 333, the lock push tube 337, the wire release tube 339, and the release wire 370. While the lengths of these elements may vary, it is preferable that the size of each relative to the others does not vary. Thus, the devices in order from longest to shortest: are as follows: release wire, release wire tube, lock push tube, and outer delivery tube.

As shown in FIG. 29, release wire loop 370a is used to engage ring 319a of hub 319 on right atrial anchor 314. Suitable alternative structures for connecting a portion of the wire 370 to the anchor 314 may be provided. Release wire 370 secures the hub 319 of right atrial anchor 314 to the delivery system 332 and permits full control of the right atrial anchor 314 to be maintained during insertion and positioning of the closure device 310 relative to the PFO track, such that the right atrial anchor 314 may be advanced and/or retracted relative to tether 316 and left atrial anchor 312 during delivery. Release wire 370 may be formed of a shape memory alloy wire, such as for example, nitinol. Release wire 370 may have a diameter of between about 0.004 inch and about 0.012 inch, and most preferably about 0.008 inches. The length of the release wire 370 is preferably between about 44.5 inch and about 50.5 inch, and most preferably about 47.5 inches. As shown in FIG. 30, release wire 370 may have a parent shape, with the looped end or release wire loop 370a extending distally from release wire tube 339. Extending proximally from release wire loop 370a, the two tails 370b of the release wire 370 extend through the release wire tube 339 to handle 380. As shown in FIG. 31d, release wire tube 339 extends into handle 380 but stops short of first knob 382a. The tail ends of release wire 370 extend out of wire release tube 339, through first knob 382a, and are connected a second actuatable element such as second knob 382b of the handle 380, as shown in FIG. 31d. As shown in FIG. 31d, at least a portion of knob 382b sits outside handle 380 in a track 381b (see FIG. 31a) such that it is accessible by a system operator. Second knob 382b is movable within the track 381b in the handle as shown in FIG. 31c. Moving knob 382b forward (distally) in its track moves release wire 370 out of the distal end of release wire tube 339, causing release wire loop 370a to extend out and away from hub 319 of the right atrial anchor 314, releasing the right atrial anchor 314. FIG. 30 illustrates the release wire 370 in an extended condition.

A method of delivering closure device 310 using delivery system 332 will now be described. Prior to deployment of closure device 310, a guide catheter (not shown) would be delivered by conventional techniques to the site of the PFO. Such conventional techniques may include the temporary use of a guide wire (not shown) and/or an obturator (not shown).

As discussed previously with respect to FIG. 14, the closure device 310 is in a collapsed condition prior to delivery, within a loading tube. The distal end of outer delivery tube 333 of the delivery system 332 sits proximal to the right atrial anchor 314. The release wire 370 secures the position of the right atrial anchor 314 relative to the delivery system 332. The right atrial anchor 314 may move along tether 316 to abut the left atrial anchor 312. This abutment allows the left and right atrial anchors 312, 314 to move in response to movement of the delivery system 332 within the guide catheter (not shown). The arms 340 of the left atrial anchor 312 may be collapsed in the distal direction, while the arms 350 of the right atrial anchor 314 may be collapsed in a proximal direction. Until second knob 382b of the handle 380 is actuated, release wire 370 is under tension, securing hub 319 to the delivery system 332.

The guide catheter is advanced to and through the PFO track and into the LA. The guide catheter extends across the PFO track. The proximal end of the guide catheter may include a hemostasis valve. The loading tube, the collapsed closure device 310, and delivery system 332 are introduced into the guide catheter through the hemostasis valve, as previously described. Movement of delivery system 332 also moves collapsed closure device 310 through the guide catheter (not shown). When fully inserted into the hemostasis valve, the distal end of the loading tube abuts the hub (not shown) of the guide catheter, preventing the loading tube from continuing to advance down the lumen of the guide catheter. The collapsed closure device 310 is then advanced out the loading tube by advancement of the delivery system 332 into the lumen of the guide catheter. Advancement of the delivery system 332 and collapsed closure device 310 continues until the closure device 310 is near the distal end of the guide catheter. The loading tube is then withdrawn out of the hemostasis valve and positioned on the delivery system 332 towards the proximal end. The hemostasis valve is then closed to stop back bleeding.

The delivery system 332 is further advanced relative to the guide catheter, deploying only the left atrial anchor 312, as previously described with respect to FIGS. 4 and 5. The left atrial anchor 312 is fully deployed from the guide catheter into the left atrium. Tether 316 extends from anchor 312 into guide catheter (not shown) and through delivery system 332. As discussed above, left atrial anchor 312 and right atrial anchor 314 are preferably self-expanding structures, expanding through a mechanical or thermal shape change, for example. Also at this point, right atrial anchor 314 remains within the delivery assembly in a collapsed state.

The delivery system 332 and guide catheter are withdrawn, pulling the left atrial anchor 312 against the opening of the PFO track. In many instances, left atrial anchor 312, with tension applied from tether 316, may mechanically close and thereby seal the PFO by bringing the septum primum (SP) into sealing contact with the septum secundum (SS). The effectiveness of this seal can be tested at this time by conventional techniques, such as contrast visualization, or a Valsalva maneuver combined with injection of bubbles, visualized with transesophageal ultrasound or intracardiac ultrasound. If the seal is ineffective, closure device 310 can be removed as has been described above, and exchanged for a different device.

The guide catheter and delivery system 332 are further withdrawn relative to the PFO track, until the distal end of the guide catheter is well within the right atrium. The right atrial anchor 314, still collapsed within the lumen of the guide catheter, moves together with the guide catheter and delivery system 332. The guide catheter, the delivery system 332, and the collapsed right atrial anchor 314 can freely slide proximally relative to the tether 316 and the left atrial anchor 312.

Once left atrial anchor 312 is positioned, right atrial anchor 314 may be deployed. Initial deployment of right atrial anchor 314 is preferably performed with the delivery system 332 and the collapsed right atrial anchor 314 withdrawn sufficiently away from left atrial anchor 312 and the right atrial septal wall, so that right atrial anchor 314 does not impinge on the wall when it initially expands. This also assures that right atrial anchor 314 will not inadvertently deploy in the PFO track or the left atrium. Because right atrial anchor 314 is not permanently attached to tether 316, anchor 314 is free to be positioned in such a location away from the right atrial septal wall.

With the guide catheter positioned in the right atrium, the right atrial anchor 314 is deployed by advancing the delivery system 332 relative to the guide catheter. This relative movement results in full deployment of right atrial anchor 314 within the right atrium RA. At this stage of the delivery method, tether 316 passes through right atrial anchor 314 and preferably extends continuously through delivery system 332 and the guide catheter to the proximal end of the handle 380. Light tension is maintained on the tether 316 from the proximal end to prevent slack on the portion of the tether 316 between the left and right atrial anchors 312, 314.

In the next step of this embodiment of a closure device delivery method, right atrial anchor 314 is advanced into contact with the right atrial septal wall. This is accomplished by advancing right atrial anchor 314 and delivery system 332 along tether 316 until right atrial anchor 314 is in a desired position relative to left atrial anchor 312, the septal wall, and the PFO, and has a desired amount of tension on left atrial anchor 312. It is preferred that left atrial anchor 312 have sufficient tension applied that the septum primum (SP) is brought into sealing apposition with the septum secundum (SS). This apposition, in many cases, may be enough to effectively close and seal the PFO. If desired, at this point in the delivery method, the effectiveness of the closure and seal can again be tested by conventional techniques, such as those described above. If the seal is ineffective, closure device 310 may be repositioned by retraction and re-advancement of delivery system 332 or closure device 310 may removed as has been described above, and exchanged for a different device (e.g., one of a different size).

The right atrial anchor 314 is advanced until it makes contact with the right atrial end of the PFO track, thus closing the track.

Up to this point, the three primary components of the delivery system 332, the outer delivery tube 333, the first inner tube or lock push tube 337, and the second inner tube or release wire tube 339, have been secured together by way of the handle 380 at the proximal end of the outer delivery tube 333, as shown in FIG. 23. The lock push tube 337 and the release wire tube 339 initially extend several cm proximally into the handle 380. At this point, both first and second knobs 382a, 382b of handle 380 remain at the proximal positions in their respective tracks 381a, 381b, as shown in FIG. 31a.

The lock 320, which is initially positioned on the tether 316, several cm proximal of the distal end of the tether 316, is now advanced distally to permanently secure the position of the right atrial anchor 314 relative to the tether 316. To advance the lock 320, the lock push tube 337 is advanced while maintaining the position of the outer delivery tube 333 and release wire tube 339 relative to the right atrial anchor 314. Advancement of lock push tube 337 in the distal direction is accomplished by moving first knob 382a distally in its track 381a on handle 380, as shown in FIG. 31b. To prevent creating slack on the tether 316, light tension is maintained at its proximal end.

The lock 320 is advanced along the tether 316 until it abuts the hub 319 of the right atrial anchor 314, as previously described. At this point, the release wire 370 is advanced to disengage the release wire loop 370a from the hub 319. Release wire 370 is advanced by moving second knob 382b of handle 380 distally in its track 381b on handle 380, as shown in FIG. 31c. Once a satisfactory closure of the PFO track is confirmed, the tether 316 may be cut at a position near the right atrial anchor 314. A cutting tool 80 may be used to perform this step, as previously described with respect to FIG. 22.

There are several points during the delivery of closure device 310 where device 310 can be completely removed from the patient. This may be necessary if, for example, device 310 is not creating a complete seal due to any of a number of causes, including, for example, the selected device being too small. When one or both anchors are deployed correctly such that they are on the correct side of the septum, the device may be retrieved or repositioned as described previously.

While it is anticipated that in the vast majority of implantations of the closure device will be complete and successful, there are rare instances where the deployment inadvertently may be done incorrectly. Such a situation may arise when both the left atrial anchor and the right atrial anchor inadvertently are deployed from the end of the guide catheter in the same chamber, i.e., either the left atrium or the right atrium. Such inadvertent deployment may be caused by many things, including for example, poor visualization of the chambers and septum, lack of operator experience, or a larger than expected PFO track, where the left atrial anchor can be pulled into the right atrium during the delivery, or the right atrial anchor can be pulled into the left atrium during delivery.

In the above described situation, when both anchors are deployed within the same chamber, it may be desirable to utilize a recapture device to facilitate recapture the anchors and position them for redeployment. Use of such a device may be preferred over independently pulling the anchors into the guide catheter. This may be true due to the fact that the right atrial anchor is movable along the tether 316, making it extremely difficult to maintain a space between the anchors as they are pulled into the guide catheter. Without the ability to maintain distance between the anchors, the anchors may come into contact with one another and brace against one another, making it difficult to collapse them.

Figure 25:
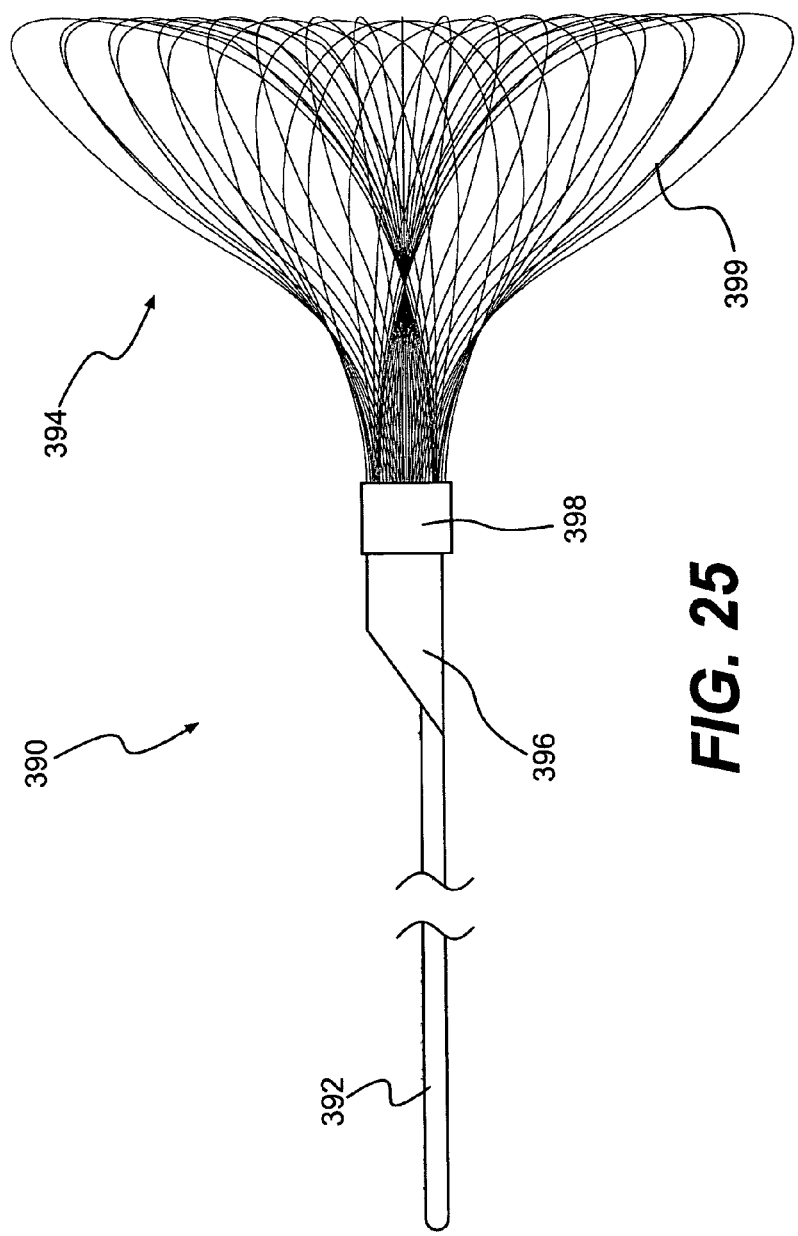
FIG. 25 is a side view of a recapture device, according to one aspect of the present invention.
Figure 26:
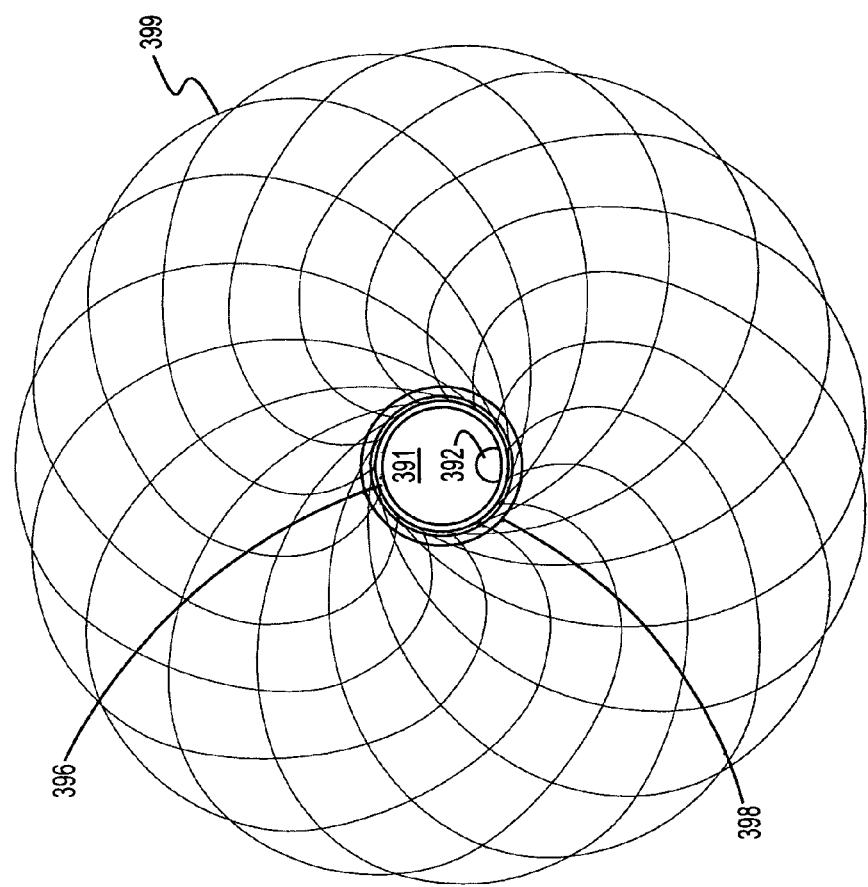
FIG. 26 is a front end view of the recapture device of FIG. 25.

According to one aspect of the present invention, a recapture device is provided. As embodied herein and shown in FIGS. 25-28, the recapture device may include a retrieval device 390. Retrieval device 390 may include a shaft 392 and an expandable retrieval portion, such as a basket portion 394. Shaft 392 may be made from any suitable material, such as, for example, a metallic wire. Shaft 392 may be coated with a lubricious material such as, for example, PTFE. The metallic wire may be stainless steel or a shape memory alloy such as nitinol. A distal end of shaft 392 is attached to a support collar 396. Shaft 392 may be attached to the support collar by any suitable means, such as, for example, welding. Support collar 396 may have a tubular or annular shape and may be made of any suitable material, such as, for example, stainless steel. As shown in FIG. 26, support collar 396 includes a central opening that forms a lumen 391 of the retrieval device to permit passage of the tether 316. If retrieval device 390 is used to capture other devices, such as implantable devices, lumen 391 may also facilitate passage of other surgical tools such as a snare, forceps, a guide wire, or other grasping devices. As shown in FIG. 25, support collar 396 may have an angled proximal end to facilitate withdrawal of the retrieval device 390 into the guide catheter 330.

As embodied herein and shown in FIGS. 25 and 26, basket portion 394 of retrieval device 390 may include a braided funnel. Use of a braided funnel of wires prevents portions of the closure device 310 from "popping" through the wires during retrieval of the closure device 310. Materials other than a braided funnel may be used for the basket portion, so long as they are suitable to prevent protrusion of the closure device through the basket portion 394. The retrieval device 390 may further include a covering (not shown) over the basket portion 394. The braided funnel may be formed by initially fabricating a length of tubular braid, for example, from a number of wires 399, for example thirty-two wires, of a shape memory alloy such as nitinol. The diameter of the tubular braid is equal to or larger than the desired final diameter of the basket portion 394 of the retrieval device 390, for example, between about 20 mm and about 30 mm, and most preferably about 25 mm. After forming the tubular braid, the tubular braid is then everted, taking one set of wire ends of the braid and folding them into the diameter of the tubular braid and bringing them adjacent to the wire ends at the opposite end of the tubular braid. All ends of the wires 399 are then positioned around the support collar 396, and then are held in position around the support collar 396 by a swage collar 398, which is then swaged in place over the wire ends. Swage collar 398 may be formed of any suitable material, such as, for example, stainless steel. The material used should have hardness that is low enough to allow radial plastic deformation to secure the ends of the wires 399 against the support collar 396.

Basket portion 394 has an expanded position and a collapsed position. Preferably, the memory position of the braided funnel is the expanded position, such that when the basket portion 394 advances out of the guide catheter 330, the basket portion 394 automatically opens to an expanded diameter.

A method of recapturing anchors 312, 314 of closure device 310 using retrieval device 390 will now be described. Although described relative to an embodiment of a closure device 310 illustrated in FIGS. 23, 24, and 28-31d, the retrieval device 390 and its method of use may be used with any other closure device described herein. Additionally, the recapture device may be used to retrieve other implantable devices inadvertently or incorrectly deployed within portions of the body, especially within chambers of the heart.

Initially, in the case of a mis-deployment of the device, both deployed anchors 312, 314 are left in place within a chamber of the heart. If still connected to hub 319 of right atrial anchor 314, release wire tube 337 is moved to release wire loop 370a from hub 319. The delivery system 332 is then removed proximally from the tether 316 and out of guide catheter 330.

Figure 27:
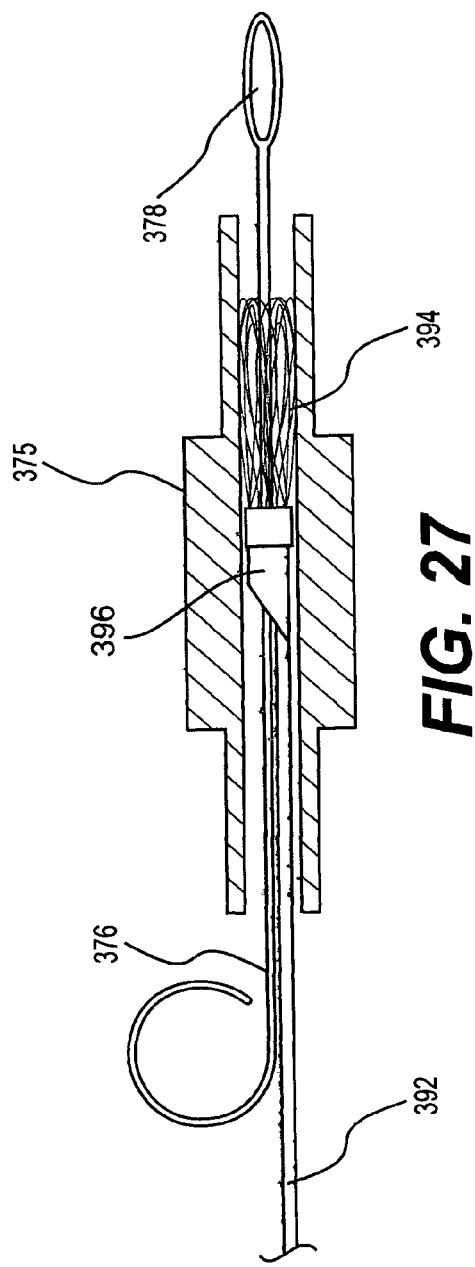
FIG. 27 is a side view of an introducer tube containing the recapture device of FIG. 25 and a threading wire, according to one aspect of the present invention.
Figure 28:
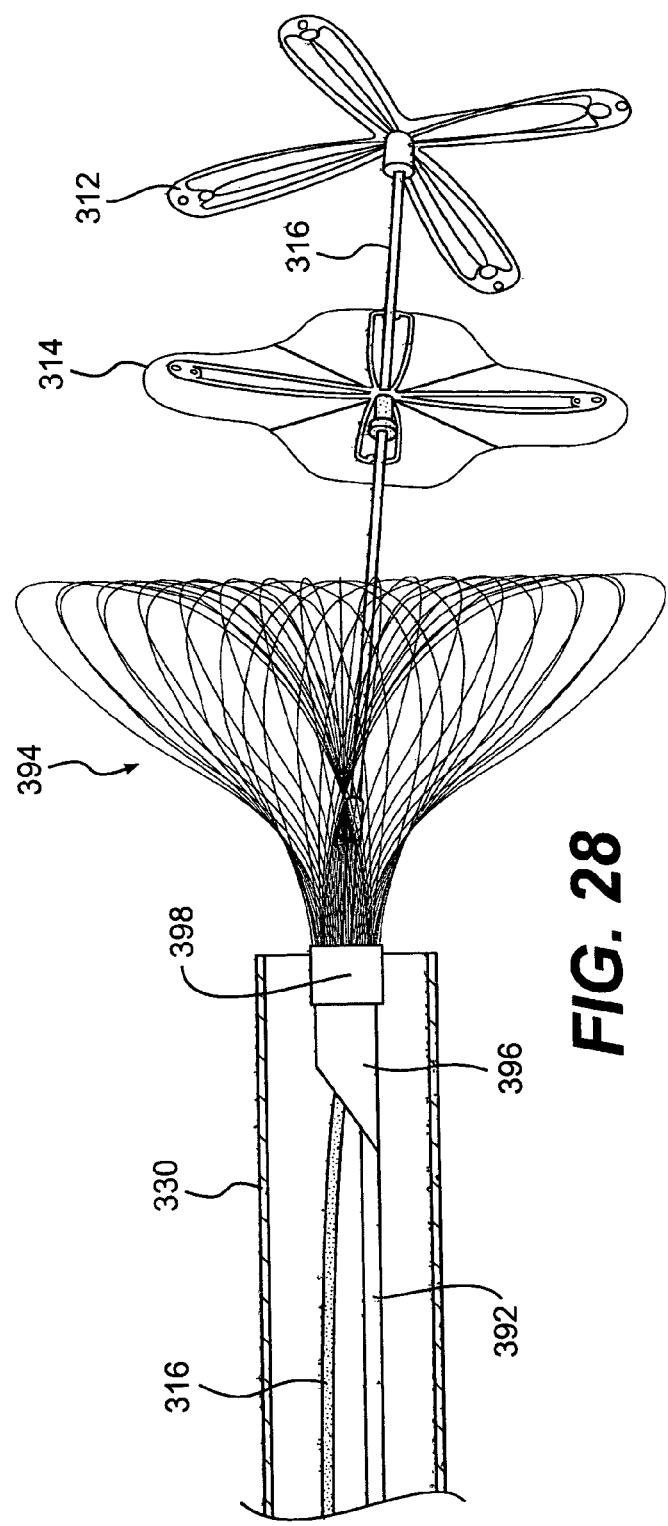
FIG. 28 is a perspective view of the recapture device of FIG. 25 advancing out of a guide catheter to retrieve a closure device, according to one aspect of the present invention.

As shown in FIG. 27, the retrieval device 390 is initially loaded into and compressed within an introducer tube 375 by advancing the introducer tube 375 distally over shaft 392 and basket portion 394. After the retrieval device 390 is positioned within introducer tube 375, a threading wire 376 is inserted through the lumen 391 of retrieval device 390, such that a distal end of the threading wire 376, which includes an eyelet 378, extends through the basket portion 394 of the retrieval device and out of the introducer tube 375. With the assembly outside of the guide catheter 330, the proximal end (not shown) of tether 316 is threaded through the eyelet 378 of threading wire 376 and pulled through the eyelet 378. The threading wire 376 is then withdrawn proximally through the retrieval device 390 and introducer tube 375, thereby pulling the tether 316 though the lumen 391 of the retrieval device 390. The tether 316 now passes longitudinally through basket portion 394 and the opening in support collar 396. The introducer tube 375 is then placed in the proximal end of the guide catheter 330 to deliver the retrieval device 390 into the lumen of the guide catheter.

The collapsed retrieval device 390 is advanced through the lumen of the guide catheter 330 until it emerges from the distal end of the guide catheter. Upon emerging from the distal end of the guide catheter 330, the basket portion 394 self-expands into its expanded memory position (see FIG. 28). Once the basket portion 394 of the retrieval device 390 expands, the right atrial anchor 314 and the left atrial anchor 312 may be pulled toward and into the basket portion 394 by pulling proximally on the tether 316. Once the anchors 312, 314 are within the basket portion 394, the tether 316 and shaft 392 of retrieval device 390 are pulled proximally relative to the guide catheter 330 to pull the retrieval device 390 and closure device into the lumen of the guide catheter 330. As the retrieval device 390 is drawn into the lumen of the guide catheter 330, the basket portion 394 collapses, thus collapsing right atrial anchor 314 and left atrial anchor 312. The collapsed basket portion 394, containing the collapsed right atrial anchor 314 and left atrial anchor 312 is withdrawn proximally into the lumen of the guide catheter 330 and then may be removed from the patient. A different closure device, for example of a different size, may then be deployed in the patient.

The various described embodiments of closure devices and methods and tools for their delivery are suitable for closure of a wide variety of PFOs. For example, PFOs with a relatively long overlap between the septum primum (SP) and septum secundum (SS) may be suitably closed, as shown in FIG. 2.

Other embodiments of the invention will be apparent to those skilled in the art from consideration of the specification and practice of the invention disclosed herein. The specification and examples are exemplary, with a true scope and spirit of the invention being indicated by the following claims.

What is claimed is:

1. An assembly for sealing a passageway in a heart, the assembly comprising:
a closure device for sealing a passageway in a heart including a first anchor adapted to be placed proximate a first end of the passageway, a second anchor adapted to be placed proximate a second end of the passageway, and a flexible elongate member adapted to extend through the passageway and connect the first and second anchors, the second anchor capable of movement relative to the elongate flexible member to vary a length of the elongate member between the first and second anchors; and
a delivery system for delivering the closure device to the passageway in the heart, the delivery system being configured to move within a lumen of a guide catheter and including a wire configured to move the second anchor along the flexible elongate member, such that movement of the wire in a first direction causes the second anchor to move relative to the first anchor towards the first anchor along the elongate member, and such that movement of the wire in a second direction causes the second anchor to move relative to the first anchor away from the first anchor along the elongate member; wherein a loop portion of the wire is configured to engage the second anchor.

2. The assembly of claim 1, wherein the passageway is a patent foramen ovale.

3. The assembly of claim 1, wherein the closure device further includes a lock movable on the flexible elongate member.

4. The assembly of claim 1, wherein the delivery system further includes a lock tube configured to move a lock along the flexible elongate member to a position adjacent the second anchor.

5. The assembly of claim 4, wherein the delivery system further includes a handle, and wherein an actuatable portion of the handle is connected to a portion of the lock tube to control movement of the lock tube.

6. The assembly of claim 4, wherein the delivery system further includes a handle having a lock tube actuator, wherein the lock tube actuator is operably connected to the lock tube such that actuation of the lock tube actuator causes movement of the lock tube along the flexible elongate member.

7. The assembly of claim 6, wherein the lock tube actuator is movable distally along the handle to cause distal movement of the lock tube.

8. The assembly of claim 1, wherein the delivery system further includes a wire tube through which the wire extends.

9. The assembly of claim 8, wherein the wire and the wire tube are configured such that advancement of the wire out of a distal end of the wire tube releases the second anchor from the wire.

10. The assembly of claim 1, wherein the delivery system further includes a handle, and wherein at least a portion of the handle is connected to a portion of the wire to facilitate release of the second anchor from the wire.

11. The assembly of claim 1, wherein the delivery system further includes a handle, and wherein an actuatable portion of the handle is connected to the wire to control movement of the wire.

12. The assembly of claim 1, further including a recapture device configured to engage the first and second anchors when the first and second anchors are deployed outside of the lumen of the guide catheter and within a chamber of the heart, the recapture device having an expanded configuration and a collapsed configuration.

13. The assembly of claim 12, wherein the recapture device includes a shaft portion and a retrieval portion, and wherein the retrieval portion is movable between the expanded configuration and the collapsed configuration.

14. The assembly of claim 1, wherein the wire is releasably connected to the second anchor.

15. The assembly of claim 1, wherein the loop portion of the wire is configured to engage a central hub of the second anchor.

16. The assembly of claim 15, wherein the loop portion of the wire is configured to engage an enlarged ring on the central hub.

17. The assembly of claim 1, wherein the delivery system further includes a handle having a wire actuator, wherein the wire actuator is operably connected to the wire such that actuation of the wire actuator causes the wire to release the second anchor.

18. The assembly of claim 17, wherein the wire actuator is movable distally along the handle to cause the loop portion of the wire to release the second anchor.

19. The assembly of claim 18, wherein the delivery system further includes a wire tube through which the wire extends, wherein distal movement of the wire actuator causes the loop portion of the wire to advance out of a distal end of the wire tube to release the second anchor from the wire.

20. The assembly of claim 1, wherein the loop portion of the wire is configured to encircle a portion of the second anchor.

21. The assembly of claim 20, wherein the loop portion of the wire is configured to encircle a central hub of the second anchor.

22. The assembly of claim 20, wherein the loop portion of the wire is configured to release the portion of the second anchor encircled by the loop portion.

23. The assembly of claim 1, wherein the loop portion of the wire is releasably connected to the second anchor.

24. An assembly for sealing a passageway in a heart, the assembly comprising:
a closure device for sealing a passageway in a heart including a first anchor adapted to be placed proximate a first end of the passageway, a second anchor adapted to be placed proximate a second end of the passageway, and a flexible elongate member adapted to extend through the passageway and connect the first and second anchors, the second anchor capable of movement relative to the elongate flexible member to vary a length of the elongate member between the first and second anchors;
a delivery system for delivering the closure device to the passageway in the heart, the delivery system being configured to move within a lumen of a guide catheter, the delivery system including:
a wire configured to control movement of the second anchor along the flexible elongate member both towards and away from the first anchor;
a lock tube configured to move a lock along the flexible elongate member to a position adjacent the second anchor; and
a wire tube through which the wire extends;
wherein the lock tube and the wire tube are arranged in a side-by-side relationship.

25. The assembly of claim 24, wherein the wire and the wire tube are configured such that advancement of the wire out of a distal end of the wire tube releases the second anchor from the wire.

26. The assembly of claim 24, wherein a loop portion of the wire is configured to engage the second anchor.

27. The assembly of claim 26, wherein the loop portion of the wire is configured to encircle a portion of the second anchor.

28. The assembly of claim 24, wherein the delivery system further includes a handle, and wherein at least a portion of the handle is connected to a portion of the wire to facilitate release of the second anchor from the wire.

29. The assembly of claim 24, wherein the wire is releasably connected to the second anchor.

30. An assembly for sealing a passageway in a heart, the assembly comprising:
- a closure device for sealing a passageway in a heart including a first anchor adapted to be placed proximate a first end of the passageway, a second anchor adapted to be placed proximate a second end of the passageway, and a flexible elongate member adapted to extend through the passageway and connect the first and second anchors, the second anchor capable of movement relative to the elongate flexible member to vary a length of the elongate member between the first and second anchors; and
- a delivery system for delivering the closure device to the passageway in the heart, the delivery system being configured to move within a lumen of a guide catheter and including a wire configured to move the second anchor along the flexible elongate member, such that movement of the wire in a first direction causes the second anchor to move relative to the first anchor towards the first anchor along the elongate member, and such that movement of the wire in a second direction causes the second anchor to move relative to the first anchor away from the first anchor along the elongate member; wherein the delivery system includes a lock tube configured to move a lock along the flexible elongate member to a position adjacent the second anchor.

31. The assembly of claim 30, wherein the passageway is a patent foramen ovale.

32. The assembly of claim 30, wherein a portion of the wire is configured to engage the second anchor.

33. The assembly of claim 32, wherein the wire is configured to engage a central hub of the second anchor.

34. The assembly of claim 33, wherein the wire is configured to engage an enlarged ring on the central hub.

35. The assembly of claim 30, wherein the delivery system further includes a handle, and wherein an actuatable portion of the handle is connected to a portion of the lock tube to control movement of the lock tube.

36. The assembly of claim 30, wherein the delivery system further includes a handle, and wherein an actuatable portion of the handle is connected to the wire to control movement of the wire.

37. The assembly of claim 30, further including a recapture device configured to engage the first and second anchors when the first and second anchors are deployed outside of the lumen of the guide catheter and within a chamber of the heart, the recapture device having an expanded configuration and a collapsed configuration.

38. The assembly of claim 37, wherein the recapture device includes a shaft portion and a retrieval portion, and wherein the retrieval portion is movable between the expanded configuration and the collapsed configuration.

39. The assembly of claim 30, wherein the delivery system further includes a handle having a lock tube actuator, wherein the lock tube actuator is operably connected to the lock tube such that actuation of the lock tube actuator causes movement of the lock tube along the flexible elongate member.

40. The assembly of claim 39, wherein the lock tube actuator is movable distally along the handle to cause distal movement of the lock tube.

41. The assembly of claim 30, wherein the delivery system further includes a handle having a wire actuator, wherein the wire actuator is operably connected to the wire such that actuation of the wire actuator causes the wire to release the second anchor.

42. The assembly of claim 41, wherein the wire actuator is movable distally along the handle to cause a portion of the wire to release the second anchor.

43. The assembly of claim 42, wherein the delivery system further includes a wire tube through which the wire extends, wherein distal movement of the wire actuator causes the portion of the wire to advance out of a distal end of the wire tube to release the second anchor from the wire.

44. The assembly of claim 30, wherein the delivery system further includes a wire tube through which the wire extends.

45. The assembly of claim 44, wherein the wire and the wire tube are configured such that advancement of the wire out of a distal end of the wire tube releases the second anchor from the wire.

46. The assembly of claim 30, wherein the delivery system further includes a handle, and wherein at least a portion of the handle is connected to a portion of the wire to facilitate release of the second anchor from the wire.

47. The assembly of claim 30, wherein the wire is releasably connected to the second anchor.

48. The assembly of claim 30, wherein a loop portion of the wire is configured to encircle a portion of the second anchor.

49. The assembly of claim 48, wherein the loop portion of the wire is configured to encircle a central hub of the second anchor.

50. The assembly of claim 48, wherein the loop portion of the wire is configured to release the portion of the second anchor encircled by the loop portion.

51. The assembly of claim 30, wherein a loop portion of the wire is releasably connected to the second anchor.

* * * * *